(12) United States Patent
Ye

(10) Patent No.: US 8,203,009 B2
(45) Date of Patent: Jun. 19, 2012

(54) NEUROTROPHIC ACTIVITY OF DEOXYGEDUNIN

(75) Inventor: Keqiang Ye, Liburn, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 13/056,377

(22) PCT Filed: Jul. 28, 2009

(86) PCT No.: PCT/US2009/051966
§ 371 (c)(1),
(2), (4) Date: Feb. 23, 2011

(87) PCT Pub. No.: WO2010/014613
PCT Pub. Date: Feb. 4, 2010

(65) Prior Publication Data
US 2011/0144096 A1   Jun. 16, 2011

Related U.S. Application Data

(60) Provisional application No. 61/084,117, filed on Jul. 28, 2008, provisional application No. 61/118,907, filed on Dec. 1, 2008.

(51) Int. Cl.
*C07D 311/00* (2006.01)
(52) U.S. Cl. ..................... 549/275
(58) Field of Classification Search .............. 549/275
See application file for complete search history.

(56) References Cited

U.S. PATENT DOCUMENTS

2008/0090897 A1* 4/2008 Steiner et al. ............. 514/453

OTHER PUBLICATIONS

Jang et al. PLoS ONE, www.plosone.org Jul. 2010 . 5(7), e11528.*

* cited by examiner

*Primary Examiner* — Nizal Chandrakumar
(74) *Attorney, Agent, or Firm* — James C. Mason; Susanne Hollinger; Emory Patent Group

(57) ABSTRACT

Novel compounds and methods for activating the TrkB receptor are provided. The methods include administering in vivo or in vitro a therapeutically effective amount of a compound containing four six-membered rings and a substituted or unsubstituted $C_5$ or $C_6$ heteroaryl or hetero-cycloalkyl ring and pharmaceutically acceptable salts, prodrugs, and derivatives thereof. Specifically, methods and compounds for the treatment of disorders including neurologic, neuropsychiatric, and metabolic disorders are provided. For example, a method is provided of treating or reducing the risk of depression, anxiety, or obesity in a subject, which includes selecting a subject with or at risk of developing depression, anxiety, or obesity, and administering to the subject a therapeutically effective amount of the described compounds. A further method of promoting neuroprotection in a subject is provided, which includes selecting a subject in need of neuroprotection, and administering to the subject a therapeutically effective amount of the described compounds.

2 Claims, 23 Drawing Sheets

Deoxygedunin 0  1  2  4  8 hr

Wb: anti-p-Trk A

Wb: anti-Trk A

Wb: anti-p-Trk B

Wb: anti-Trk B

Wb: anti-Tubulin

NEUROTROPHIC ACTIVITY OF DEOXYGEDUNIN

This application claims the benefit of U.S. Provisional Application Ser. No. 61/084,117, filed Jul. 28, 2008, and 61/118,907, filed Dec. 1, 2008. The entire disclosures of the prior applications are hereby incorporated by reference.

This invention was made with government support under Grant No. R01-NS045627 from the National Institutes of Health. The government has certain rights in this invention.

BACKGROUND

Neurologic and neuropsychiatric disorders such as depression, anxiety, amyotrophic lateral sclerosis, and central nervous system injuries, to name a few, afflict millions of people every year resulting in a multitude of symptoms including weight change, decreased energy, headaches, digestive problems, chronic pain, paralysis, and in certain instances, death.

One class of growth factors proposed as a treatment for neurologic and neuropsychiatric disorders are neurotrophins, which include brain-derived neurotrophic factor (BDNF). BDNF is believed to have neurotrophic action on various neuronal populations including sensory neurons, motor neurons, dopaminergic neurons of the substantia nigra, and cholinergic neurons of the basal forebrain, which are involved in several neurologic and neuropsychiatric disorders. Preclinical evidence indicates that BDNF might be useful as a therapeutic agent for various neurologic and neuropsychiatric disorders; however, the in vivo instability of such a peptide based therapy limits its usefulness.

Neurotrophins are also indicated in metabolic disorders. Mutations in the tyrosine kinase receptor trkB or in one of its natural ligands, e.g., BDNF or neurotrophin-4 (NT4), are known to lead to severe hyperphagia and obesity in rodents and humans. Administration of trkB ligands such as BDNF or NT4 have been shown to suppress appetite and body weight in a dose-dependent manner in several murine models of obesity. Accumulating evidence indicates that TrkB signaling directly modulates appetite, metabolism, and taste preference. TrkB agonists thus emerge as potential therapeutics for metabolic disorders.

SUMMARY

Novel compounds and methods for the treatment of disorders including neurologic disorders, neuropsychiactric disorders (e.g., anxiety or depression), and metabolic disorders (e.g., obesity) are provided. The methods include administering to a subject a therapeutically effective amount of a compound having the following formula:

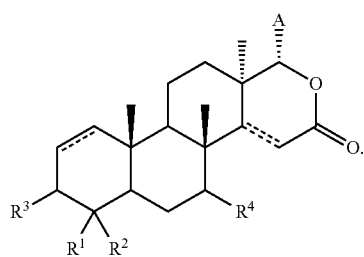

or a pharmaceutically acceptable salt or prodrug thereof. In this compound, $R^1$ and $R^2$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; $R^3$ is hydrogen, carbonyl, hydroxyl, —O—$R^1$, —O—C(=O)—$R^1$, or —N$R^5R^6$, wherein $R^5$ and $R^6$, are each independently selected from $R^1$; $R^4$ is carbonyl, —$R^1$, —O—$R^1$, or —O—C(=O)—$R^1$; A is a substituted or unsubstituted $C_5$ or $C_6$ heteroaryl or $C_5$ or $C_6$ ====== heterocycloallyl; is a single or double bond, wherein two double bonds are not adjacent; and ====== is a double bond or

A first method for the treatment of disorders including neurologic disorders, neuropsychiactric disorders, and metabolic disorders using this compound is related to treating or reducing the risk of depression, anxiety, or obesity in a subject, which includes selecting a subject with or at risk of developing depression, anxiety, or obesity, and administering to the subject a therapeutically effective amount of the compound described above or a derivative thereof. A further method of promoting neuroprotection in a subject is provided, which includes selecting a subject in need of neuroprotection, and administering to the subject a therapeutically effective amount of the compound described above or a derivate thereof.

A method of activating a TrkB receptor on a neuron also is provided. The method includes providing the neuron with a TrkB receptor, then contacting the TrkB receptor in vitro with the compound described above or a derivate thereof in an amount sufficient to activate the TrkB receptor. The neuron can be, for example, a mammalian cell.

The details of one or more examples of the compounds and methods are set forth in the accompanying drawings and the description below. Other features, objects, and advantages will be apparent from the description and drawing, and from the claims.

DETAILED DESCRIPTION

Figure 1:
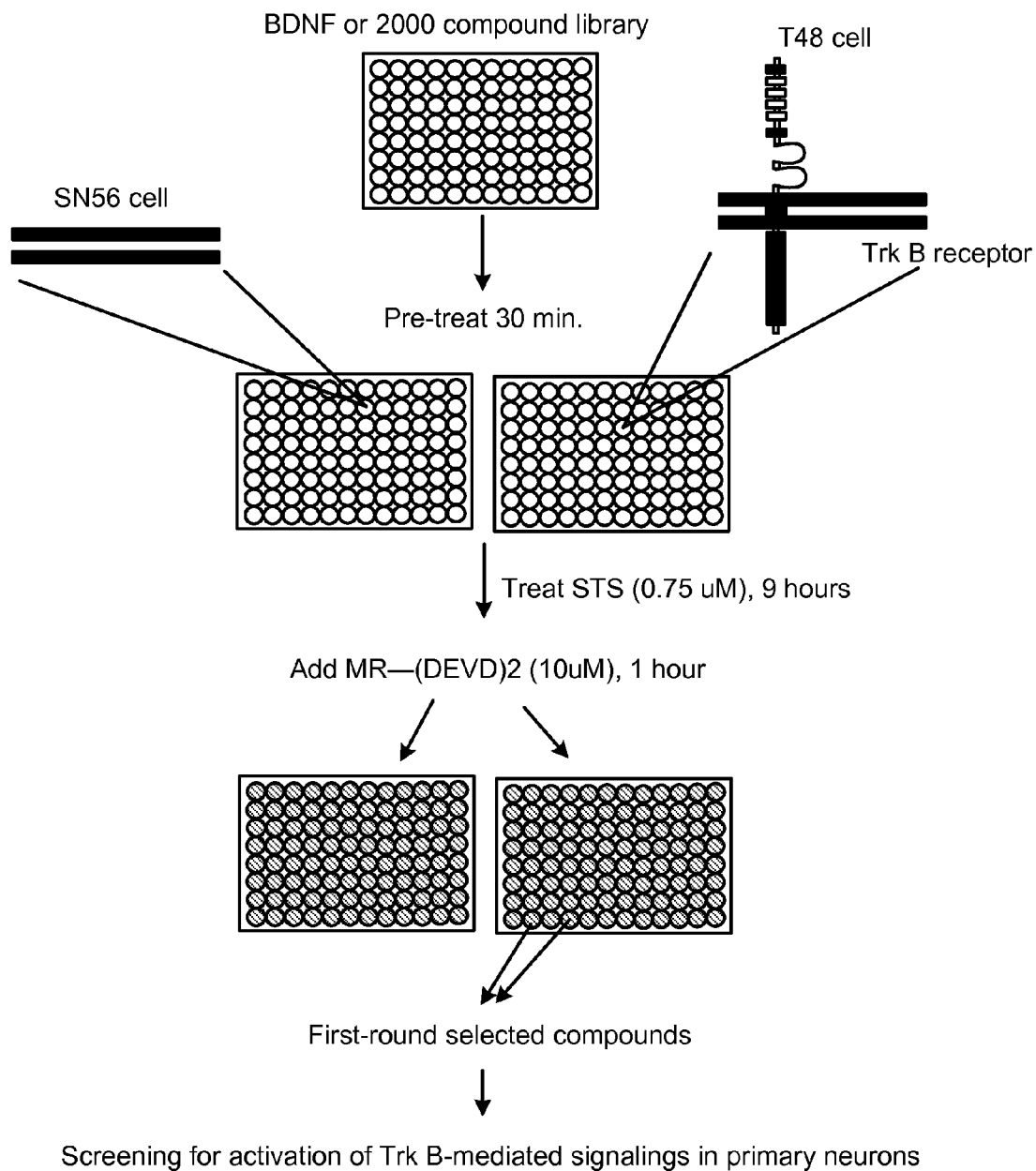
FIG. 1 shows a design for a chemical screen to identify TrkB agonists.

Described herein are compounds and methods for the activation of the TrkB receptor. These compounds and methods are effective in the treatment of diseases and illnesses associated with the activation of the TrkB receptor including neurological disorders, neuropsychiatric disorders, and metabolic disorders. Examples of neurological and neuropsychiatric disorders include depression, anxiety, Alzheimer's, CNS injuries, and the like. Examples of metabolic disorders include obesity and hyperphagia. Specifically, provided herein are compounds containing four six-membered rings and a substituted or unsubstituted $C_5$ or $C_6$ heteroaryl or $C_5$ or $C_6$ heterocycloalkyl ring and pharmaceutically acceptable salts, prodrugs, and derivatives thereof. Methods of their use in the treatment of depression, anxiety, obesity, other neurological disorders, and the like also are described herein.

The compounds containing four six-membered rings and a substituted or unsubstituted $C_5$ or $C_6$ heteroaryl or $C_5$ or $C_6$ heterocycloalkyl ring are represented by Compound I:

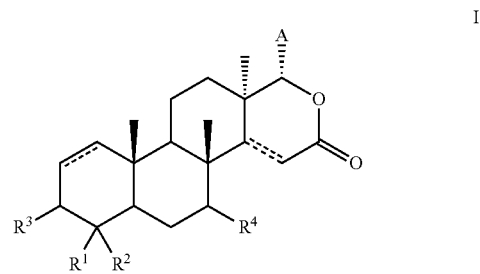

and pharmaceutically acceptable salts and prodrugs thereof.

In Compound I, $R^1$ and $R^2$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, e.g., phenyl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl. $R^1$ and $R^2$ each can be, for example, methyl.

In Compound I, $R^3$ is hydrogen, carbonyl, hydroxyl, —O—$R^1$, —O—C(=O)—$R^1$, or —NR$^5$R$^6$, wherein $R^5$ and $R^6$, are each independently selected from $R^1$.

Additionally, in Compound I, $R^4$ is hydrogen, carbonyl, —R$^1$, —O—R$^1$, or —O—C(=O)—R$^1$. $R^4$ can be, for example, —O—C(=O)—CH$_3$.

Also in Compound I, A is a substituted or unsubstituted $C_5$ or $C_6$ heteroaryl or $C_5$ or $C_6$ heterocycloalkyl. A can be, for example,

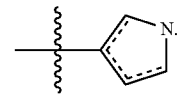

Additionally, A can be substituted with halogen, —OR % or —NR$^5$R$^6$. For further example, A can be

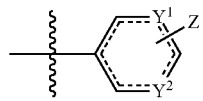

wherein $Y^1$ and $Y^2$ are each independently O, N, S, or CH$_2$; and Z is hydrogen, halogen, —OR$^4$, or —NR$^5$R$^6$. Also, for example, A can be

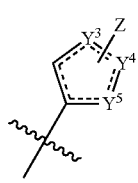
wherein $Y^3$, $Y^4$, and $Y^5$ are each independently O, N, S, or $CH_2$; and Z is hydrogen, halogen, —$OR^4$, or —$NR^5R^6$. Further examples of A include:
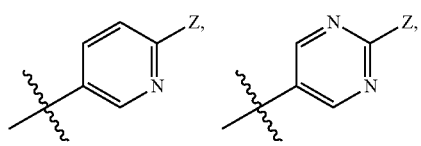
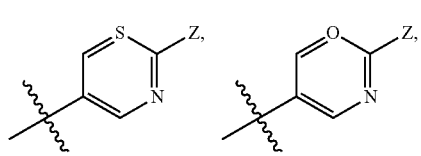
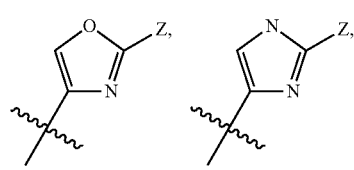
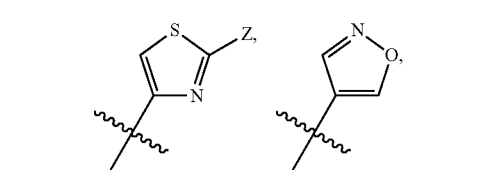
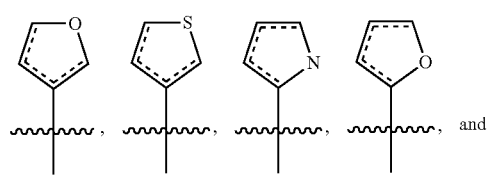, and
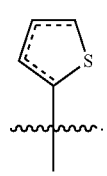.
Further, in Compound I, "=====" is a single or double bond, wherein two double bonds are not adjacent, and "⋯⋯" is a double bond or
.
Additional, non-limiting, examles of Compound I include:
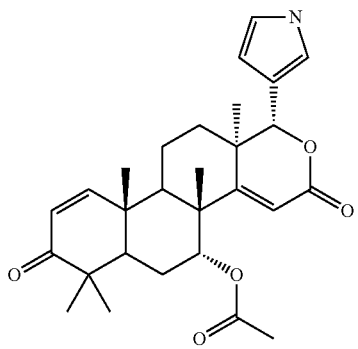
I-1
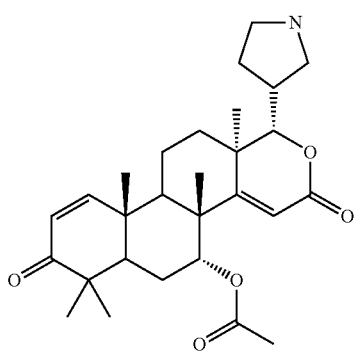
I-2
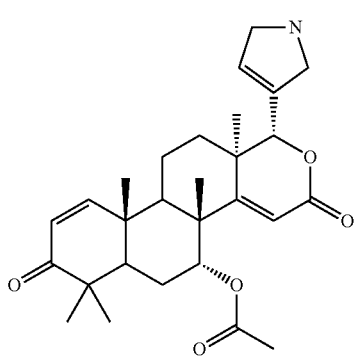
I-3
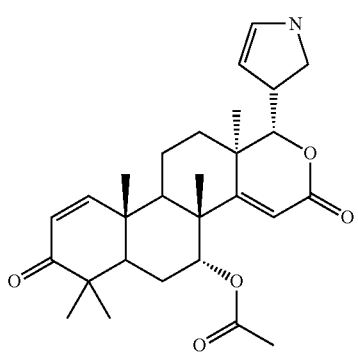
I-4

-continued
I-5
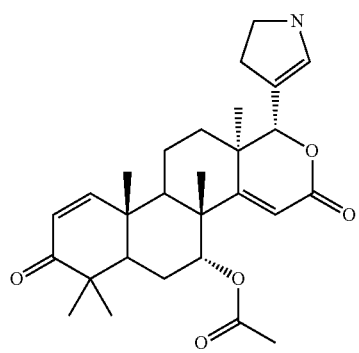
I-6
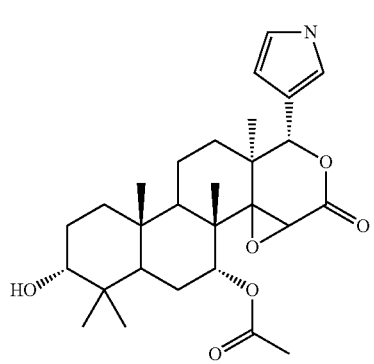
I-7
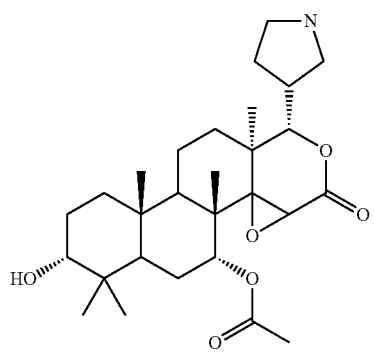
I-8
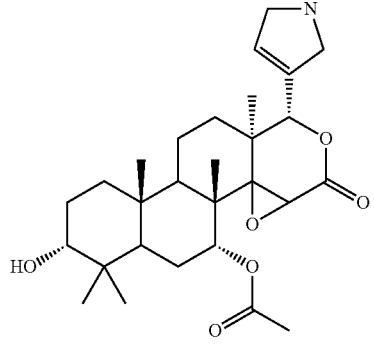
-continued
I-9
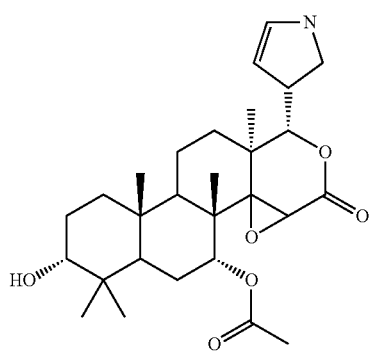
I-10
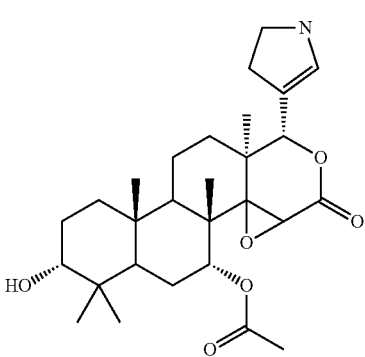
I-11
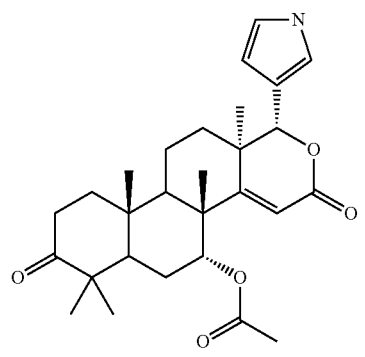
I-12
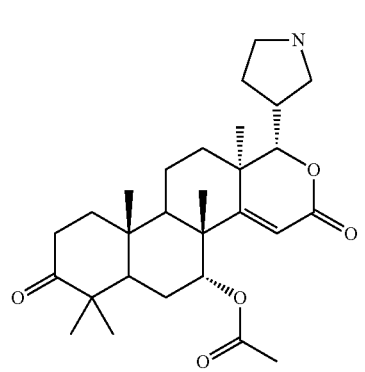

I-13
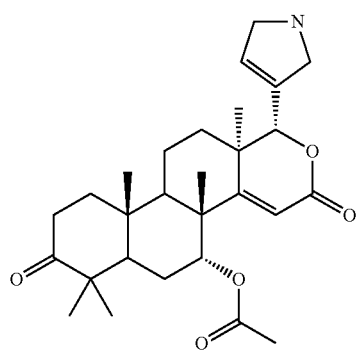
I-14
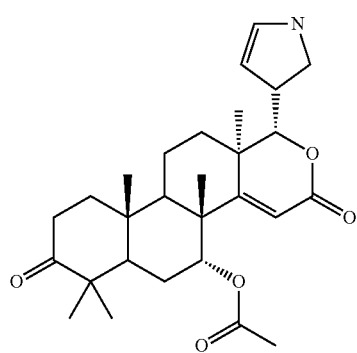
I-15
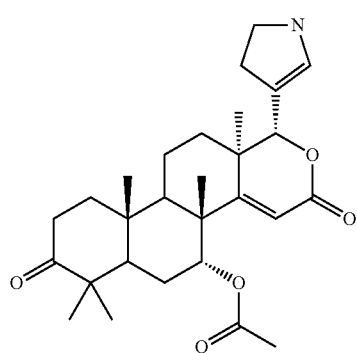
I-16
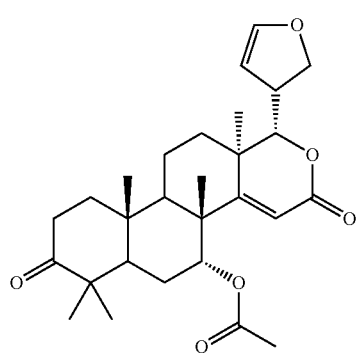
I-17
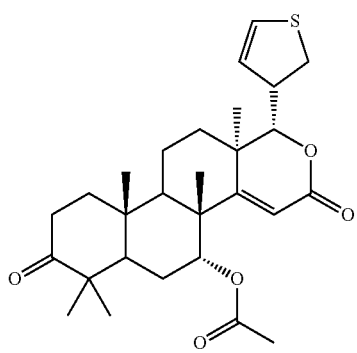
I-18
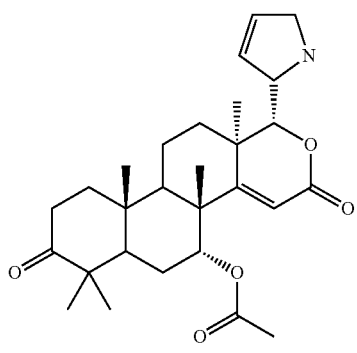
I-19
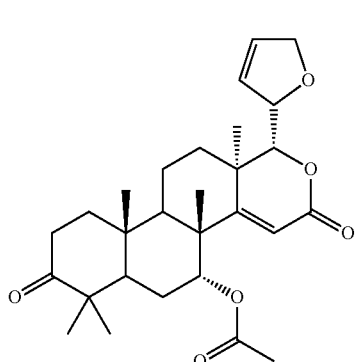
I-20
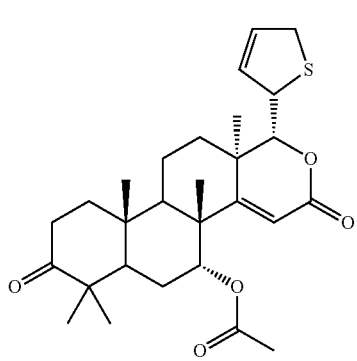

I-21
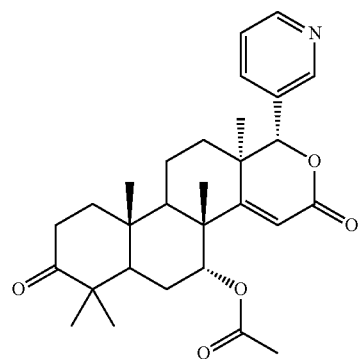
I-22
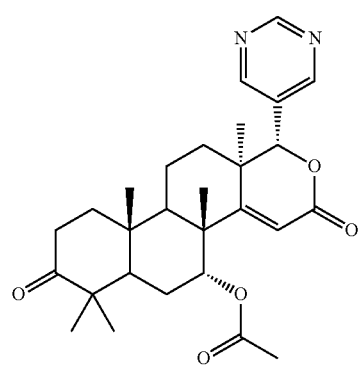
I-23
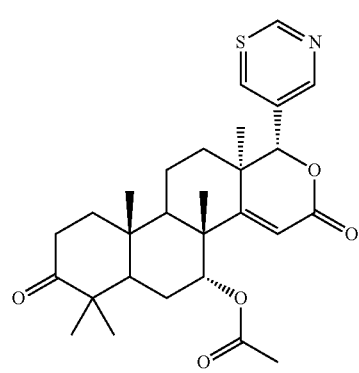
I-24
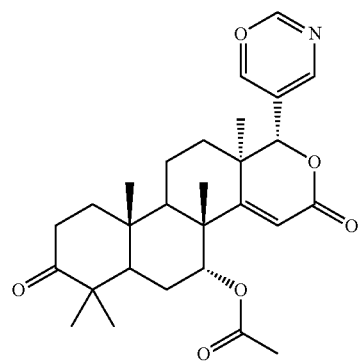
I-25
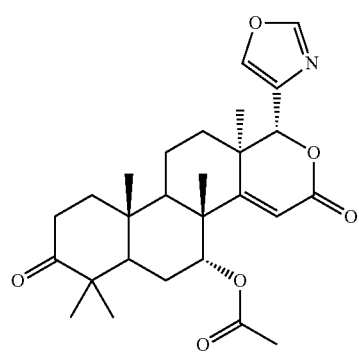
I-26
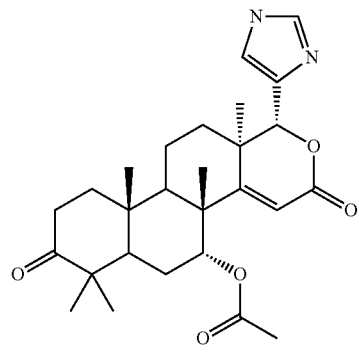
I-27
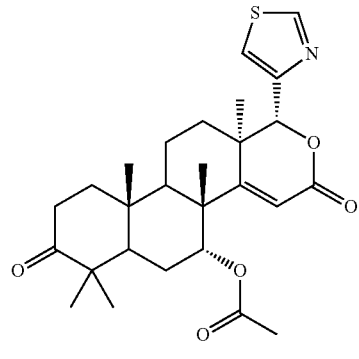
I-28
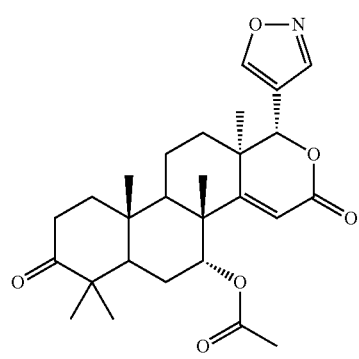

I-29 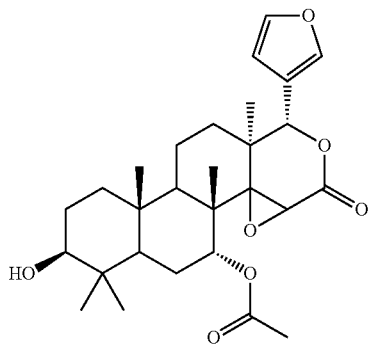

I-30 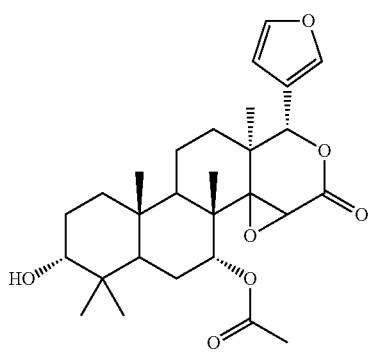

I-31 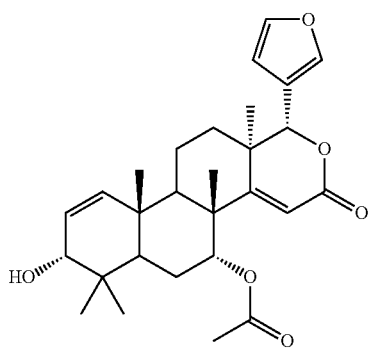

I-32 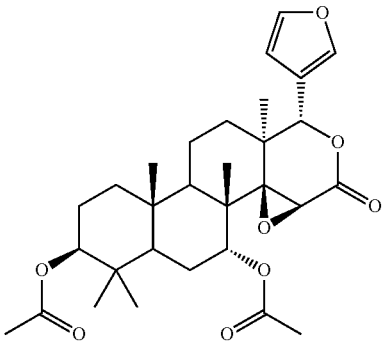

I-33 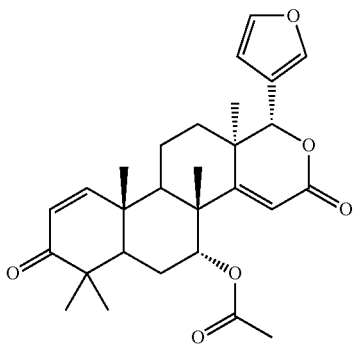

The compounds described herein can be prepared in a variety of ways known to one skilled in the art of organic synthesis or variation thereon as appreciated by those skilled in the art. The compounds described herein can be prepared from readily available starting materials. Optimum reaction conditions may vary with the particular reactants or solvents used, but such conditions can be determined by one skilled in the art.

Variations on Compound I include the addition, subtraction, or movement of the various constituents as described for each compound. Similarly, when one or more chiral centers is present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

As used herein, the terms alkyl, alkenyl, and alkynyl include straight- and branched-chain monovalent substituents. Examples include methyl, ethyl, isobutyl, 3-butynyl, and the like. Heteroalkyl, heteroalkenyl, and heteroalkynyl are similarly defined but may contain O, S or N heteroatoms or combinations thereof within the backbone. The term substituted indicates the main substituent has attached to it one or more additional components, such as, for example, OH, halogen, or one of the substituents listed above.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatograpy (HPLC) or thin layer chromatography.

The methods described herein include a method of treating or reducing the risk of disorders associated with activation of the TrkB receptor including neurological disorders, neuropsychiatric disorders, and metabolic disorders in a subject. Examples of neurological and neuropsychiatric disorders include depression, anxiety, Alzheimer's, CNS injuries, and the like. Examples of metabolic disorders include obesity and hyperphagia. This method includes the steps of selecting a subject with or at risk of developing the neurological disorder, neuropsychiatric disorder, or metabolic disorder, and administering to the subject an effective amount of Compound I or derivative thereof as described herein. The Compound I or derivative thereof as described herein can be administered systemically (e.g., orally, parenterally (e.g. intravenously), intramuscularly, intreperitoneally, transdermally (e.g., by a patch), extracorporeally, topically, by inhalation, subcutaneously or the like), by administration into the central nervous system (e.g., into the brain (intracerebrally or intraventricularly), spinal cord, or into the cerebrospinal fluid), or any combination thereof.

Also provided is a method of promoting neuroprotection in a subject. This method includes the steps of selecting a subject in need of neuroprotection, and administering to the subject an effective amount of Compound I or derivative thereof as described herein. A subject in need of neuroprotection can, for example, be a subject that has amyotrophic lateral sclerosis (ALS) or a central nervous system injury. A central nervous system injury includes, for example, a brain injury, a spinal cord injury, or a cerebrovascular event (e.g., a stroke).

Methods can further comprise testing the effectiveness of Compound I or derivative thereof as described herein. Testing the effectiveness can include, but is not limited to, imaging (e.g., Magnetic Resonance Imaging (MRI)) and functional measurements (e.g., survival or clinical symptoms like analysis of speech patterns, logic, comprehension, memory, mood, and orientation). The method optionally further comprises adjusting the dosage or treatment regimen of Compound I or derivative thereof as described herein.

Further provided is a method of activating a TrkB receptor on a neuron (e.g., a mammalian neuron). This method includes the steps of providing a neuron with a TrkB receptor, and contacting the TrkB receptor in vitro with Compound I or derivative thereof as described herein in an amount sufficient to activate the TrkB receptor. Also provided is a method of screening for an agent that potentiates the TrkB receptor activation. The screening method includes activating the TrkB receptor on a neuron as described and contacting the neuron with the agent to be screened. An enhanced effect indicates the agent potentiates the effect of Compound I or derivative thereof as described herein.

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compounds described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing significant unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's. Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing Compound I or derivative thereof as described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of Compound I or derivative thereof as described herein include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as filler's in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of Compound I or derivative thereof as described herein include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include adjuvants, such as wetting, emulsifying, suspending, sweetening, flavoring, or perfuming agents. Adjuvants include, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of Compound I or derivative thereof as described herein for rectal administrations are preferably suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The term pharmaceutically acceptable salt as used herein refers to those salts of Compound I or derivative thereof as described herein that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of Compound I or derivative thereof as described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Berge et al., *J. Pharm. Sci.* (1977) 66:1-19, which is incorporated herein by reference in its entirety, at least, for compositions taught herein.)

The compounds described above or derivatives thereof are useful in treating disorders associated with activation of the TrkB receptor including neurological disorders, neuropsychiatric disorders, and metabolic disorders (e.g., obesity), as well as for promoting neuroprotection in humans, e.g., including pediatric and geriatric populations, and animals, e.g., veterinary applications. A subject in need of neuroprotection is a subject at risk for or having a neurologic or neuropsychiatric disorder. Neurologic or neuropsychiatric disorders include, for example, depression, anxiety, amyotrophic later sclerosis, Alzheimer's disease, Huntington's disease, Rett syndrome, epilepsy, Parkinson's disease, and central nervous system injuries. Central nervous system injuries include, for example, spinal cord injury, stroke, hypoxia, ischemia, and brain injury. As used herein the terms promoting, treating, and treatment includes prevention; delay in onset; diminution, eradication, or delay in exacerbation of one or more signs or symptoms after onset; and prevention of relapse.

The methods and compounds as described herein are useful for both prophylactic and therapeutic treatment. For prophylactic use, a therapeutically effective amount of Compound I or derivative thereof as described herein are administered to a subject prior to onset (e.g., before obvious signs of neurologic or neuropsychiatric disorder), during early onset (e.g., upon initial signs and symptoms of neurological disorder), or after an established neurological disorder. Prophylactic administration can occur for several days to years prior to the manifestation of symptoms of a neurological or neuropsychiatric disorder. Prophylactic administration can be used, for example, in the preventative treatment of subjects diagnosed with genetic neurological disorders such as Huntington's disease or prior to surgery in which stroke or hypoxia is a risk. Therapeutic treatment involves administering to a subject a therapeutically effective amount of Compound I or derivative thereof as described herein after a disorder, e.g., a neurological disorder, neuropsychiatric disorder, or metabolic disorders (e.g., obesity), is diagnosed.

Administration of Compound I or derivative thereof as described herein can be carried out using therapeutically effective amounts of Compound I or derivative thereof as described herein for periods of time effective to treat neurological disorders. The effective amount of Compound I or derivative thereof as described herein may be determined by one of ordinary skill in the art and includes exemplary dosage amounts for a mammal of from about 0.5 to about 100 mg/kg of body weight of active compound per day, which may be administered in a single dose or in the form of individual divided doses, such as from 1 to 4 times per day. Alternatively, the dosage amount can be from about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

In these methods, the disorder being treated, e.g., depression, anxiety, central nervous system injury, obesity, or other disorder, can be further treated with one or more additional agents. The one or more additional agents and Compound I or derivative thereof as described herein can be administered in any order, including simultaneous administration, as well as temporally spaced order of up to several days apart. The methods may also include more than a single administration of the one or more additional agents and/or Compound I or derivative thereof as described herein. The administration of the one or more additional agent and Compound I or derivative thereof as described herein may be by the same or different routes and concurrently or sequentially. When treating with one or more additional agents, Compound I or derivative thereof as described herein can be combined into a pharmaceutical composition with the one or more additional agents. For example, Compound I or derivative thereof as described herein can be combined into a pharmaceutical composition with an anti-depressant, such as, for example imipramine, fluoxetine, paroxetine, and/or sertraline. As a further example, Compound I or derivative thereof as described herein can be combined into a pharmaceutical composition with an anti-anxiolytic, such as, for example diazepam, alprazolam, clonazepam, and/or hydroxyzine.

The examples below are intended to further illustrate protocols for assessing the methods and compounds described herein, and are not intended to limit the scope of the claims.

EXAMPLES

General Methods

Cells, Reagents and Mice

For Examples 1 to 8, human neuroblastoma SH-SY5Y and human embryonic kidney HEK293 cell lines are grown in DMEM with 10% fetal bovine serum (FBS) and 100 units penicillin-streptomycin at 37° C. with 5% $CO_2$ atmosphere in a humidified incubator. Mouse septal neuron x neuroblastoma hybrids SN56 cells are created by fusing N18TG2 neuroblastoma cells with murine (strain C57BL/6) neurons from postnatal 21 days septa. The SN56 cells are maintained at 37° C. with 5% $CO_2$ atmosphere in DMEM medium containing 1 mM pyruvate and 10% FBS. T48 and T62 cells, to be stably transfected with rat TrkB, are cultured in the same medium containing 300 µg/ml G418.

For Examples 9 to 16, SN56 cells were maintained at 37° C. with 5% $CO_2$ atmosphere in DMEM medium containing 1 mM pyruvate and 10% FBS. T48 and T62 cells, which were stably transfected with rat TrkB, were cultured in the same medium containing 300 µg/ml G418. NGF and BDNF were from Roche Diagnostics Corporation (Indianapolis, Ind.). Phospho-Akt-473 or 308, Akt antibodies, anti-phospho-Erk1/2, and anti-phospho-TrkA Y490 were from Cell Signaling Technology, Inc. (Danvers, Mass.). Anti-TrkA antibody was from Santa Cruz Biotechnology, Inc. (Santa Cruz, Calif.). Anti-TrkB antibody was from BioVision, Inc. (Mountain View, Calif.). Anti-p-TrkB Y817 antibodies were from Epitomics, Inc. (Burlingame, Calif.). The chemical library containing 2000 biologically active compounds was from the Spectrum Collection (MicroSource Discovery System, Inc. Gaylordsville, Conn. 06755). TrkBF616A mice have been described previously (Chen et al., 2005). TrkBF616A mice, TrkB +/−, TrkA +/− and BDNF +/−C57BL/6 mice were bred in a pathogen-free environment. [$^3$H]-Acetic acid, sodium salt (specific activity: 75-150 mCi/mmol; concentration: 10 mCi/mL) was purchased from PerkinElmer, Inc. (Waltham, Mass.). Deoxygedunin was purchased from Gaia Chemical Corporation (Gaylordsville, Conn.). All other chemicals were purchased from Sigma-Aldrich Co. (St. Louis, Mo.) or Alfa Aesar (Ward Hill, Mass.).

Primary Rat Cortical Neuron Culture

Unless specifically described, primary cultured rat cortical neurons are prepared as follows. E17 rat pups are decapitated and cortex is extirpated, cross chopped, and suspended by pipetting for separation in 5% fetal calf serum (FCS), 5% horse serum (HS) DMEM. The cell suspension then is centrifuged at 250×g for 5 minutes. This operation is repeated. Cells are seeded into polyethyleneimine-coated 10 cm$^2$ dishes and 12-well plates including coated-coverslips and are incubated at 37° C. in 5% $CO_2$/95% air. After 3 hours, the culture medium is changed to Neurobasal containing B-27 supplement (Invitrogen; Carlsbad, Calif.) and is incubated for 4 days. For maintenance, half of the culture medium is changed to fresh Neurobasal/B27 every 4 days. After 1 week, the dished cultured neurons is ready for use.

Immunofluorescent Staining

Unless specifically described, primary hippocampal neurons are seeded on poly-L lysine coated coverslips in a 12-well plate. After 7 days in vitro, the neurons are treated with 100 ng/ml BDNF or variety of flavone compounds (1 µM) for 30 minutes, and then are washed with PBS. Cells are fixed with 3% formaldehyde in PBS at room temperature for 10 minutes. The cells then are permeabilized and blocked by 0.4% Triton X-100 and 2% FBS in PBS at room temperature for 15 minutes, are washed with PBS three times, and are treated with anti-MAP2 (1:200) and anti-phospho-TrkB antibodies (1:500). After staining with FITC- or Rhodamine-conjugated secondary antibody, the coverslips are mounted on slides. Fluorescent images are taken by a fluorescence microscope.

Immunohistochemstry Staining

Unless specifically described, brain tissues are fixed in 4% paraformaldehyde overnight followed by paraffin embedding. Sections of 5 µm are cut. For immununohistochemical staining, brain sections are deparaffinized in xylene and rehydrated in graded alcohols. Endogenous peroxidase activity are blocked by 3% hydrogen peroxide for 5 minutes and all slides are boiled in 10 mM sodium citrate buffer (pH 6.0) for 10 minutes. Phosphorylated Trk A, Trk A, phosphorylated Trk B, and Trk B are detected using specific antibodies and, e.g., a Zymed HistostainPlus AEC kit (Invitrogen; Carlsbad, Calif.). Slides then are counterstained with hematoxylin.

Preparation of 32-[$^3$H]$_3$-deoxygedunin.

[$^3$H]-Acetic acid, sodium salt (11 µmol, 0.17 mL, 0.17 mL of ethanol solution) was syringed into a heavy-walled glass vial bearing a magnetic stirrer. The ethanol was removed under vacuum and replaced with 0.5 mL of THF at 0° C. Isobutylchloroformate (3.0 µL, 23 µmol) was then added and the reaction mixture was stirred for one hour at 0° C. A solution of 7-deacetyldeoxygedunin (5 mg, 11 µmop, prepared by acetyl deprotection of deoxgedunin with $K_2CO_3$ in MeOH, in 0.5 mL THF was then added dropwise. The reaction was stirred for one hour. Solvent was then removed under vacuum and the product was purified by preparative thin layer chromatography (SiO$_2$; 1:1 EtOAc:hexanes) to give 3 mg (58%) of 32-[$^3$H]$_3$-deoxygedunin. Deoxygedunin was prepared under identical reaction conditions prior to preparation of 32-[$^3$H]$_3$-deoxygedunin in order to confirm product formation.

TrkB dimerization Assay

HEK293 cells transfected with GST-TrkB and HA-TrkA or TrkB were washed once in PBS, and lysed in 1 ml lysis buffer (50 mM Tris, pH 7.4, 150 mM NaCl, 1 mM EDTA, 0.5% Triton X-100, 1.5 mM Na3VO4, 50 mM NaF, 10 mM sodium pyrophosphate, 10 mM sodium (3-glycerophosphate, 1 mM phenylmethylsulfonyl flouride (PMSF), 5 mg/ml aprotinin, 1 mg/ml leupeptin, 1 mg/ml pepstatin A), and centrifuged for 10 minutes at 14,000×g at 4° C. The supernatant was then transferred to a fresh tube and transfected TrkB receptor was pulled down with glutathione beads. The coprecipitated proteins were resolved on SDS-PAGE. The samples were transferred to a nitrocellular membrane, and immunoblotting analysis was performed with a variety of antibodies.

Binding Constant Determination

Purified TrkB ECD or ICD proteins (10 ug/each) were incubated with different [$^3$H-deoxygedunin] in 1 ml binding buffer (0.05 M Na/K phosphate buffer (pH 7.1), 200 mM NaCl) (1 nM [$^3$H] deoxygedunin ~82300 cpm) at 4° C. for 10 minutes. After incubation, the reaction mixture was loaded on filter paper and washed with 3×5 ml Tris buffer (100 mM Tris, pH 7.1). The dried filter paper was put into a small vial and subjected to liquid scintillation counter analysis. The value of the dissociation constant and the number of sites were obtained from Scatchard plots by using the equation $r/[L]$ free$=n/Kd-r/Kd$, where r is the ratio of the concentration of bound ligand to the total protein concentration and n is the number of binding sites.

Cortex-Specific BDNF Deletion

The Cortex-Specific Cre mouse line was previously described as "transgenic line C" (Chhatwal et al., Gene Ther. 14, 575-583 (2007)). Briefly, coding sequence for Cre-recombinase (Cre-IRES-DsRed2) was placed downstream of a 3 kb cholecystokinin (CCK) promoter, linearized, purified, and microinjected into the pronuclei of one-cell C57/BL6 embryos, which were then implanted into pseudopregnant C57/BL6 females. Following verification of gene expression in the different transgenic lines (Chhatwal et al., Nat. Neurosci. 9, 870-872 (2006)), the cortex-specific "line C" was crossed to a floxed-stop lacZ reporter mouse line (Soriano, Nat. Genet., 21, 70-71 (1999)) as well as the floxed BDNF mouse line (Rios et al., Mol. Endocrinol., 15, 1748-1757 (2001)). Region specific Cre gene expression and BDNF deletion were confirmed with in situ hybridization, x-gal staining for (3-galactosidase expression, and Western blot for BDNF protein levels.

Vestibular Ganglion Dissection in BDNF −/− Pups

The cochleae of various drug-treated pups (P1 or P2 BDNF +/+ and −/− pups) were first fixed through cardioperfusion of 4% paraformaldehyde (in PBS). Each cochlea was dissected out and postfixed in 1% osmium for one hour at room temperature. Samples were decalcified in 0.35 M EDTA (pH 7.5, in PBS) for 72 hours at 4° C., followed by gradual dehydration in graded alcohols, infiltrated, and embedded in epoxy resin with the conventional protocols. Consecutive cochlear sections (5 μm in thickness) were cut with a microtome (Microm HM335E, GmbH) along the axis of the modiolus. Sections were stained with toluidine blue. Vestibular ganglions were identified by their location in the auditory internal meatus with the basal cochlear turn and the cochlear modiolus as morphological reference landmarks.

Focal Ischemia Model

A total of 12 rats were used (1 rat was excluded because of inadequate reperfusion). Focal cerebral ischemia was induced by occlusion of the right middle cerebral artery as described by Sayeed et al., Ann. Emerg. Med. 47, 381-389 (2006). Drug Administration: The rats subjected to MCAO incurring ischemic insult <40% of baseline LDF were randomly assigned to receive either deoxygedunin (n=4), 7,8-DHF (n=4), or vehicle (n=4) treatment. Deoxygedunin and 7,8-DHF were given at the dose of 5 mg/kg by i.p. injection 5 minutes prior to the onset of reperfusion. Rats in the vehicle group underwent the same experimental protocol, except that they received an identical volume/weight of vehicle only. Statistical analysis: All results are expressed as mean±S.E.M. Mean ischemic lesion volume were analyzed using the Student's t-test. The criterion for statistical significance was set at $p<0.05$.

Mouse Conditioned Fear Studies

Following a two-day habituation to testing context, wild-type C57B1/6J mice (N=28, male, 8-10 weeks old) were fear conditioned in eight identical startle response systems (SR-LAB, SDI) consisting of a nonrestrictive Plexiglas cylinder, 5.5 cm in diameter and 13 cm long, mounted on a Plexiglas platform which was located in a ventilated, sound-attenuated chamber. One hour prior to fear conditioning, mice received 8-OH-Deoxygedunin (N=14, 5 mg/kg, i.p.) or vehicle (N=14, 17% DMSO in PBS). Mice then received 5 tone—footshock pairings, with 30 second 12 kHz, 85 dB tones which co-terminated with the footshocks (intensity of 0.5 mA, 0.5 second) with a 5 minute intertrial interval (ITI), after which they were returned to their homecage. 24 and 48 hrs after training, the mice were tested for freezing in rodent modular test chambers with an inside area of 30.5 cm×24.1 cm×21.0 cm. Three minutes after placing the mouse in the test chamber, fifteen 30 second conditioned stimulus (CS) tones with an ITI of 1.5 min were delivered through a high-frequency speaker attached to the side of each chamber. Percentage time spent freezing during the CS presentations was calculated for each mouse using FreezeFrame (Product Number: ACT-100) (Coulbourn Instruments, Whitehall, Pa.).

Example 1

Cell-Based Screen to Identify Compounds that Protect TrkB Expressing Cells from Apoptosis To create and test reporter cell lines. In order to identify small molecules that mimic BDNF and activate TrkB, TrkB stably transfected murine cell lines are created. The T48 and T62 cell lines are created by transfecting basal forebrain SN56 cells, which express negligible TrkB, with a TrkB expression construct. To test expression of TrkB, the cells are treated with BDNF, which is predicted to result in strong phosphorylation of Trk-490 and Akt activation in comparison to the TrkA NTR stably expressing T17 cell line indicating expression of TrkB. To test resistance to apoptosis, the SN56 cells and the T48 cell line are either untreated or treated with BDNF, and then are subjected to an apoptotic assay. The apoptotic assay involves treating the cells with 0.75 uM Staurosporine for 9 hours, and 1 hour before completing the experiment, the cells are treated with 10 μM MR (DEVD)$_2$. The cells then are fixed with 4% paraformaldehyde for 15 minutes, washed with phosphate buffered saline (PBS), and incubated with Hoechst 33342 for 10 minutes. Cover slides are washed with PBS, mounted, and then the cells are examined using a fluorescent microscope to see which cells turn red upon caspase cleavage.

Cell-based screen. To screen Compound I and derivatives thereof, a cell-based apoptic assay is used. The screen employs a cell permeable fluorescent dye, MR (DEVD)$_2$, which turns red upon caspase cleavage in apoptotic cells. SN56 and T48 cells, which are created as described above, are plated at 10,000 cells per well in multiple 96-well plates and are exposed to Compound I and derivatives thereof for 30 minutes at a concentration of 10 μM in DMSO. Following exposure to the compounds, the cells are subjected to the developed fluorescent apoptotic assay described above (method schematically shown in FIG. 1).

Candidates that selectively protect the T48 cell line, but not the SN56 cell line, then are subjected to a neurite outgrowth assay of SH-SY5Y cells for a secondary screen. Any positive compounds, i.e., identified active compounds, are further validated for TrkB activation, PI-3 kinase/Akt and MAP kinases signaling cascade activation in primary hippocampal neurons.

Example 2

Identification of Survival Enhancers

To compare the apoptosis inhibitory activity of identified active compounds, the compounds are preincubated with SN56 and T48 cells, and subsequently are subjected to the fluorescent apoptotic assay as described above. To examine whether these identified active compounds promote neuronal survival, hippocampal neurons are prepared and the cultures are pretreated with the identified active compounds for 30 minutes, followed by treatment with 50 μM glutamate for 16 hours. A quantitative apoptosis assay, for example, demonstrates the effectiveness of any active compounds.

To explore whether the identified active compounds exert a protective effect on hippocampal neurons in Oxygen-Glucose Deprivation (OGD), primary preparations of neurons are treated with BDNF or various flavone derivatives for 30 minutes prior to OGD. After 3 hours, apoptotic analysis demonstrates whether an active compound has a protective effect. Further, a titration assay reveals whether an active compound protects neurons in a dose-dependent manner.

Example 3

Protocol to Determine Whether an Identified Active Compound Triggers TrkB Activation in Hippocampal Neurons In Vitro BDNF binding to TrkB induces its autophosphorylation and, subsequently, activation of downstream kinase pathways including MAPK and PI3/Akt. To explore whether an identified active compound triggers TrkB activation, immunofluorescent staining on hippocampal neurons with anti-phospho TrkB antibody is conducted. To examine whether an identified active compound stimulates TrkB-mediated downstream signaling cascades, Western analysis is performed and the activation of Akt and Erk also is monitored. To test whether the stimulatory effect of an identified active compound is mediated through TrkB, cells are either untreated or treated with K252a, a selective inhibitor of the tyrosine kinase activity of the Trk family of neutrophin receptors. Cells treated with K252a block TrkB tyrosine phosphorylation in cells exposed to an identified active compound. To probe the time course of TrkB activation triggered by an identified active compound, hippocampal neurons are treated with an identified active compound at 500 nM and phosphorylation of Erk and Akt is determined over time by Western analysis. Whether stimulation of Erk and Akt by an identified active compound occurs in a dose dependent manner also is determined.

Example 4

Protocol to Determine Whether an Identified Active Compound Triggers TrkB Activation in Hippocampal Neurons In Vivo To assess whether an identified active compound provokes TrkB activation in the brain, mice are intraperitoneally injected with a dose of 5 mg/kg and analyzed at various time points. Western analysis reveals whether TrkB, but not TrkA, is selectively phosphorylated in the brain after injection. Further, whether the protein and mRNA levels of the neurotrophic receptors is altered after treatment with an identified active compound is measured. Immunofluorescent staining of the brain displays substantial TrkB phosphorylation in the hippocampus for an active compound.

Example 5

Protocol to Determine Whether an Identified Active Compound Binds the Extracellular Domain of the TrkB Receptor BDNF is known to bind the TrkB receptor and provoke its dimerization (Barbacid, J. Neurobiol., 25:1386-1403, 1994; Klein et al, Cell, 66:395-403, 1991). To explore whether an identified active compound triggers TrkB receptor dimerization, HEK293 cells are cotransfected with GST-TrkB and HA-TrkB or HA-TrkA. The cells then are treated with BDNF or an identified active compound (0.5 μM) for 30 minutes. The cells then are harvested, washed once in PBS, and lysed in 1 ml lysis buffer (50 mM Tris, pH 7.4, 150 mM NaCl, 1 mM EDTA, 0.5% Triton X-100, 1.5 mM Na$_3$VO$_4$, 50 mM NaF, 10 mM sodium pyrophosphate, 10 mM sodium O-glycerophosphate, 1 mM phenylmethylsulfonyl fluoride (PMSF), 5 mg/ml aprotinin, 1 mg/ml leupeptin, 1 mg/ml pepstatin A) and are centrifuged for 10 minutes at 14,000×g at 4° C. The supernatant is transferred to a fresh tube and transfected TrkB receptor is separated from the supernatant with glutathione beads, and the coprecipitated proteins are resolved on SDS-PAGE. The samples are transferred to nitrocellular membrane, and Western analysis demonstrates whether the identified active compound provoked TrkB dimerization to a similar manner as BDNF.

To determine if an identified active compound promotes tyrosine phosphorylation of the other Trk receptors, HEK293 cells are transfected with various Trk receptors, which is followed by treatment with the identified active compound. Treatment with an identified active compound that elicits tyrosine phosphorylation in the TrkB receptor but not in the TrkA or TrkC receptor indicates an active compound.

To determine whether an identified active compound physically and directly binds to the TrkB receptor, in vitro binding assays can be conducted with purified TrkB extracellular domain (ECD) and intracellular domain (ICD) recombinant proteins. Purified TrkB ECD and ICD (10 μg of each) are incubated with different concentrations of $^3$H-labeled identified active compound in 1 ml of binding buffer (0.05M Na/K. phosphate buffer, pH 7.1, 200 mM NaCl) at 4° C. for 10 minutes. After the incubation, the reaction mixture is loaded on filter paper. The mixture is washed three times with Tris buffer (100 mM Tris, pH 7.1), and the dried filter paper is put into a small vial and subjected to liquid scintillation counter analysis. Gradual increments of [$^3$H]-labeled identified active compound indicate progressively bound TrkB ECD but not ICD. The value of the dissociate constant and the number of sites will then be obtained from Scatchard plots using the equation r/[L]$_{free}$=n/K$_d$-r/K$_d$, where r is the ratio of the concentration of bound ligand to the total protein concentration and n is the number of binding sites. Quantitative analysis using the Scatchard plot reveals whether the ratio of ligand to the receptor is 1:1 and the binding constant K$_d$.

To further explore the association of an identified active compound and the TrkB receptor, an in vitro binding assay can be performed. Increasing volumes of GST-TrkB ECD and GST-TrkB ICD are bound to glutathione beads to a total of 250 uL, and 500 nM identified active compound in 250 μl (20% DMSO/80% PBS) are incubated with the beads in the column at 4° C. for 30 minutes. After the incubation, the elute fractions are collected and the concentration of eluted identified active compound is analyzed by UV-spectrometry at a wavelength of 410 nm.

BDNF is known to bind to the region of the TrkB ECD that contains the third leucine-rich motif (LRM), the second cysteine cluster (CC) domain, and the Immunoglobulin 2 (Ig2) domain (Haniu et al., J. Biol. Chem., 272:25296-303, 1997). To map where an identified active compound binds on the TrkB ECD, truncation mutants of the ECD is made and in vitro binding assays are conducted. From association data obtained from the truncated mutants, the binding regions are determined.

Example 6

Protocol to Determine Whether an Identified Active Compound Prevents Kainic Acid-Triggered Neuronal Apoptosis and Decreases Infarct Volume of Stroked Rat Brain Kainic acid (KA) is a potent agonist for the AMPA receptor. Peripheral injections of KA result in recurrent seizures and the subsequent degeneration of select populations of neurons in the hippocampus (Schauwecker and Steward, Proc. Natl. Acad. Sci. USA, 94:4103-8, 1997). KA induces neuronal cell death in a caspase-dependent and independent manners (Faherty et al., Brain Res. Mol. Brain. Res., 70:159-63, 1999; Glassford et al., Neurol. Res., 24:796-800, 2002; Liu et al., Mol. Cell, 29:665-78, 2008). To explore whether an identified active compound blocks the neurotoxicity initiated by KA, C57BL/6 mice aged 60 days are intraperitoneally injected with either a single dose of 20% DMSO in saline, 20 mg/kg KA, or 5 mg/kg of an identified active compound followed by 20 mg/kg of KA. After 5 days, the mice are anesthetized, perfused with 4% paraformaldehyde in 0.1 M phosphate buffered saline, and the brains are removed, postfixed overnight, and processed for paraffin embedding. Serial sections of the brain are cut to a thickness of 5 μm and mounted on slides. TUNEL staining reveals whether KA provokes apoptosis in the hippocampus, which is diminished by an active compound.

To further determine the neuroprotective potential in vivo, an identified active compound can be tested in a transient middle cerebral artery occlusion (MCAO) stroke model in adult male rats. Focal cerebral ischemia is induced by occlusion of the right middle cerebral artery as previously described (Sayeed et al, Ann. Emerg. Med., 47:381-9, 2006). After 2 hours MCAO followed by reperfusion, the animals receive vehicle or an identified active compound (5 mg/kg) intraperitoneally 5 minutes prior to the onset of reperfusion. Survival of the ischemic insult after treatment with an identified active compound demonstrates neuroprotection. Further, brain slices stained with 2,3,5-triphenyltetrazolium chloride (TTC) 24 hours after MCAO in vehicle-treated and identified active compound-treated rats indicate a neuroprotective effect.

Example 7

Protocol to Determine Whether an Identified Active Compound Protects Neurons from Apoptosis in TrkB Dependent Manner To determine whether an identified active compound selectively activates TrkB receptor and prevents neuronal cell death, cortical neurons are prepared from homozygous pups of TrkB +/− mice, which are mated to the same genotype. The activation of TrkB and down stream indicators of TrkB activation, such as Capase-3, are monitored. To further assess whether an identified active compound blocks neuronal apoptosis in a TrkB dependent manner, cortical neurons are prepared from homozygous pups of TrkC +/− mice, which are mated to the same genotype. Again, the activation of TrkB and down stream indicators of TrkB activation, such as Capase-3, are monitored.

To explore whether the neuroprotective action of an identified active compound is dependent on TrkB activation in vivo, TrkB F616A knockin mice are used. The TrkB F616A receptor has been shown to be selectively blocked by 1NMPP1 inhibitor and lead to TrkB-null phenotypes (Chen et al., Neuron, 46:13-21, 2005). To further assess whether an identified active compound can mimic BDNF, cortical neurons are prepared from TrkB F616A knockin mice. The cortical neurons are pretreated for 30 minutes with either K252a Trk tyrosine kinase inhibitor (100 nM) or 1NMPP1 inhibitor (100 nM) followed by 0.5 μM identified active compound for 30 minutes. Whether TrkB phosphorylation is selectively blocked by 1NMPP1, is monitored.

To determine if 1NMPP1 makes neurons treated with an identified active compound vulnerable to KA-provoked neuronal cell death, TrkF616A knockin mice are fed with 1NMPP1 (25 mM) in drinking water one day prior to pharmacological reagent treatment. The next day, the mice are intraperitoneally injected with KA (25 mg/kg), or an identified active compound (5 mg/kg) 4 hours prior to KA injection. The control mice are injected with either KA or an identified active compound alone, or the mice are administered an identified active compound 4 hours before KA. After 4 days, the mice are sacrificed and the brains are homogenized and ultracentrifuged. The supernatant then is employed for SDS-PAGE and immunoblotting analysis. Whether the identified active compound suppresses KA-provoked apoptosis, i.e., exhibits a neuroprotective effect, is determined.

Example 8

Protocol to Determine Whether an Identified Active Compound Displays an Anti-Depressive Effect BDNF has been shown to play an essential role in mediating antidepressants' therapeutic effects (Castren, Curr. Opin. Pharmacol., 4:58-64, 2004; Duman, Biol. Psychiatry, 56:140-5, 2004; Groves, Mol. Psychiatry, 12:1079-88, 2007; Monteggia et al., Proc. Natl. Acad. Sci. USA, 101:10827-32, 2004; Saarelainen et al., J. Steroid Biochem. Mol. Biol., 78:231-9, 2003). Further, infusion of exogenous BDNF into hippocampus or brain stem has been shown to have an anti-depressant-like behavioral effect (Shirayama et al., J. Neurosci., 22:3251-61, 2002; Siuciak et al., Pharmacol. Biochem. Behav., 56:131-7, 1997). To explore whether an identified active compound has an antidepressant effect like BDNF, a forced swim test is conducted. Adult male mice (2-3 months old) are randomly submitted, without a pre-swim, to a forced swim test of 6 minutes with immobility recorded in the last 4 minutes. The mice are injected intraperitoneally for 5 days with saline, imipramine (20 mg/kg), amitryptyline (15 mg/kg), or an identified active compound (5 mg/kg). The mice are allowed to adapt to the test room for 2 days, and the mice are placed in a clear glass cylinder with a diameter of 16 cm, half-filled with clear water at 24° C. The water depth of 14 cm does not allow the mice to reach the bottom of the cylinder, and the water is changed after each mouse. Mice treated with an identified active compound exhibiting an anti-depressive effect show increased mobility.

Example 9

Identification of Gedunin Derivatives as Survival Enhancers

Figure 2:
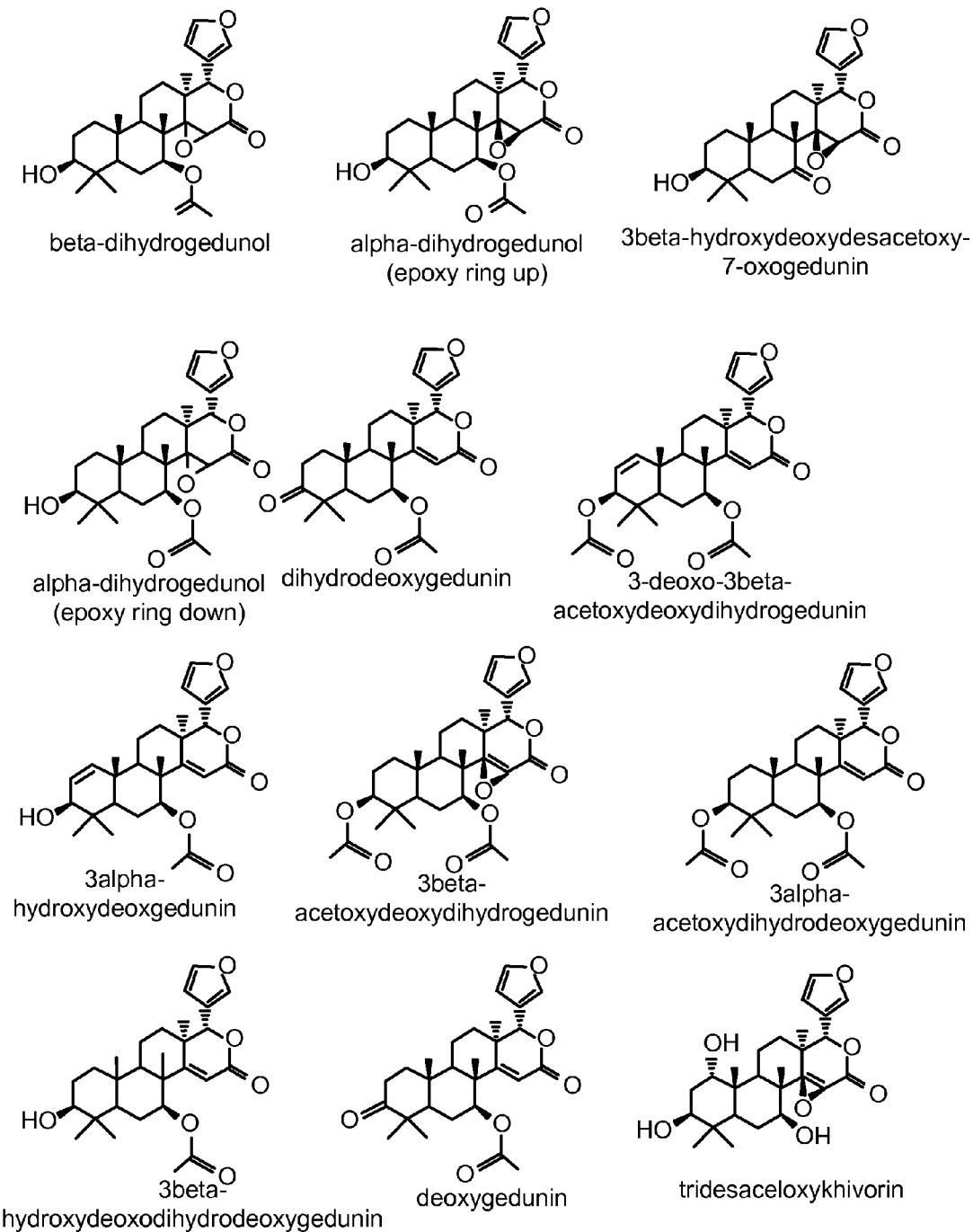
FIG. 2 shows the chemical structures of 12 gedunin related compounds.
Figure 3:
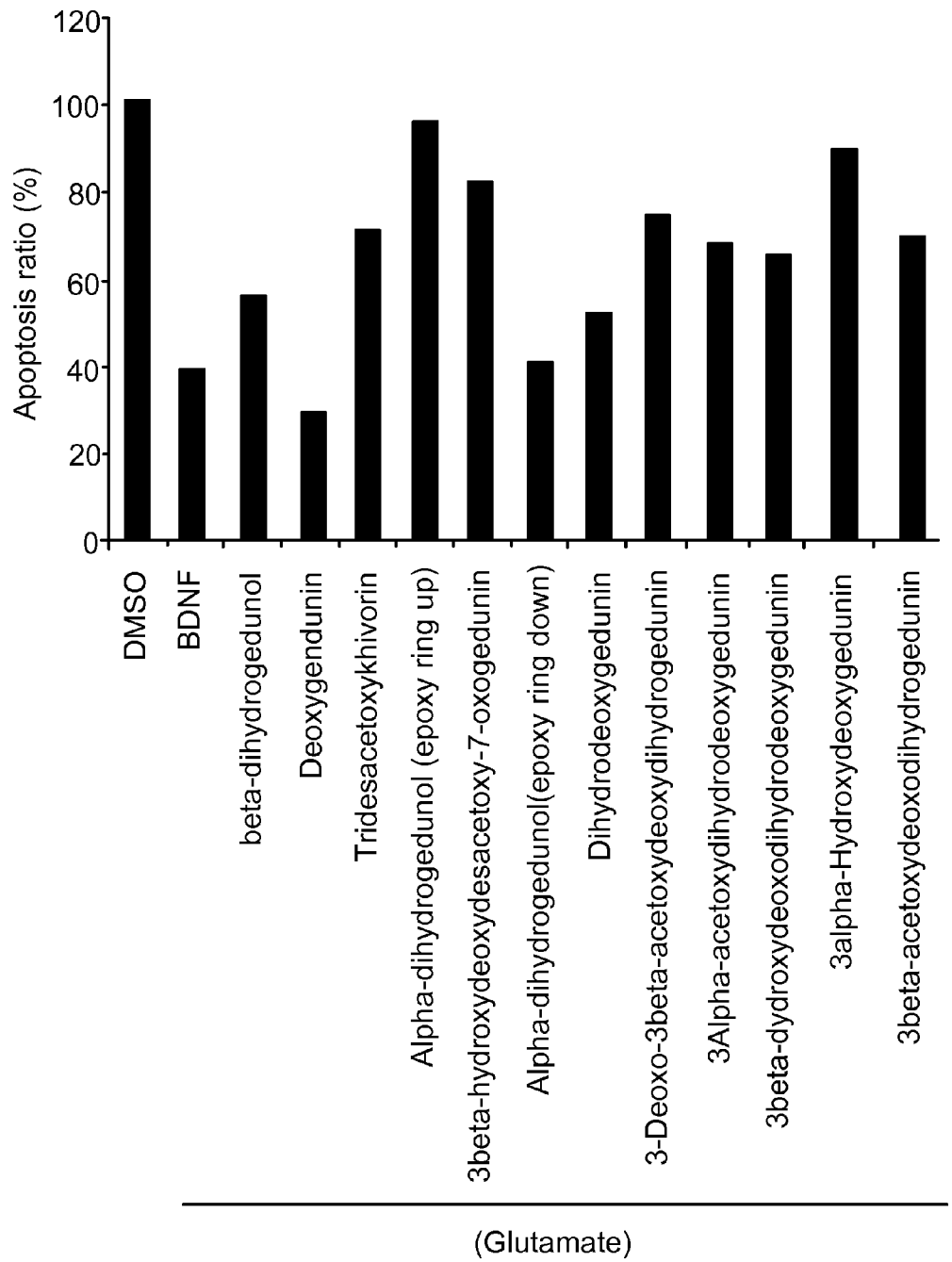
FIG. 3 shows the results of an apoptosis inhibitory assay for the 12 gedunin related compounds from FIG. 2.
Figure 4:
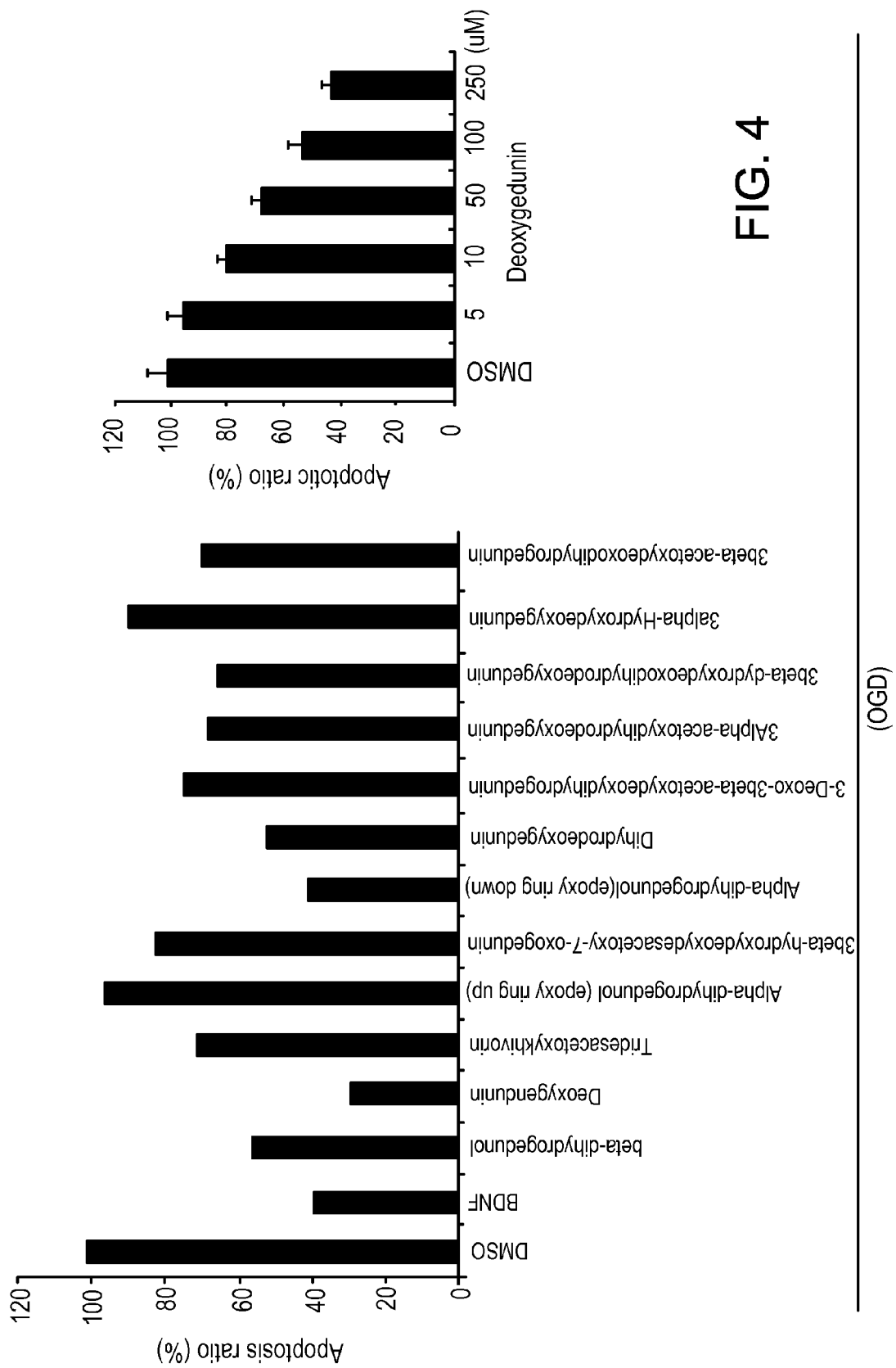
FIG. 4 shows the results of an apoptosis inhibitory assay under oxygen-glucose-deprivation conditions (left panel) and a titration assay for deoxygedunin under the same conditions for the 12 gedunin related compounds from FIG. 2.

Using a cell-based screen as described above in Example 1 (based on the anti-apoptotic action of TrkB signaling) and the chemical library from the Spectrum Collection (described above), 66 positive hits were generated, four of which were gedunin derivatives. The Spectrum Collection library also contained numerous gedunin derivatives, which did not generate hits. The chemical structures of 12 gedunin related compounds contained in the Spectrum Collection library (including both hits and non-hits) are shown in FIG. 2. To compare apoptosis inhibitory activity, each of these compounds (0.5 µM) was preincubated with hippocampal neurons for 30 min, followed by 50 µM glutamate for 16 h. Among the 12 gedunin derivatives (see FIG. 3), deoxygedunin (1-33) displayed the most robust protective effect, followed by alphadihydrogedunol (epoxy ring down) (1-30) and dihydrodeoxygedunin (1-16). In this assay, neurons with both cleaved caspase (MR (DEVD)2 red cells) and condensed nuclei (DAPI staining) were counted as apoptotic cells. As discussed above in Example 2, OGD (Oxygen-Glucose Deprivation) was used an in vitro model for ischemic stroke. Apoptotic ratio was compared to neurons treated with BDNF which was known to reduce ischemic injury (Kurozumi et al., 2004; Schabitz et al., 2000) and DMSO which has no protective effect. Deoxygedunin, alpha-dihydrogedunol (epoxy ring down) and dihydrodeoxygedunin exhibited potent protective effects on hippocampal neurons under OGD (see FIG. 4, left panel). As shown in FIG. 4, right panel, a titration assay shows that deoxygedunin protects neurons in a dose-dependent manner.

Example 10

Deoxygedunin Activates TrkB and Protects Neurons from Apoptosis

Figure 5:
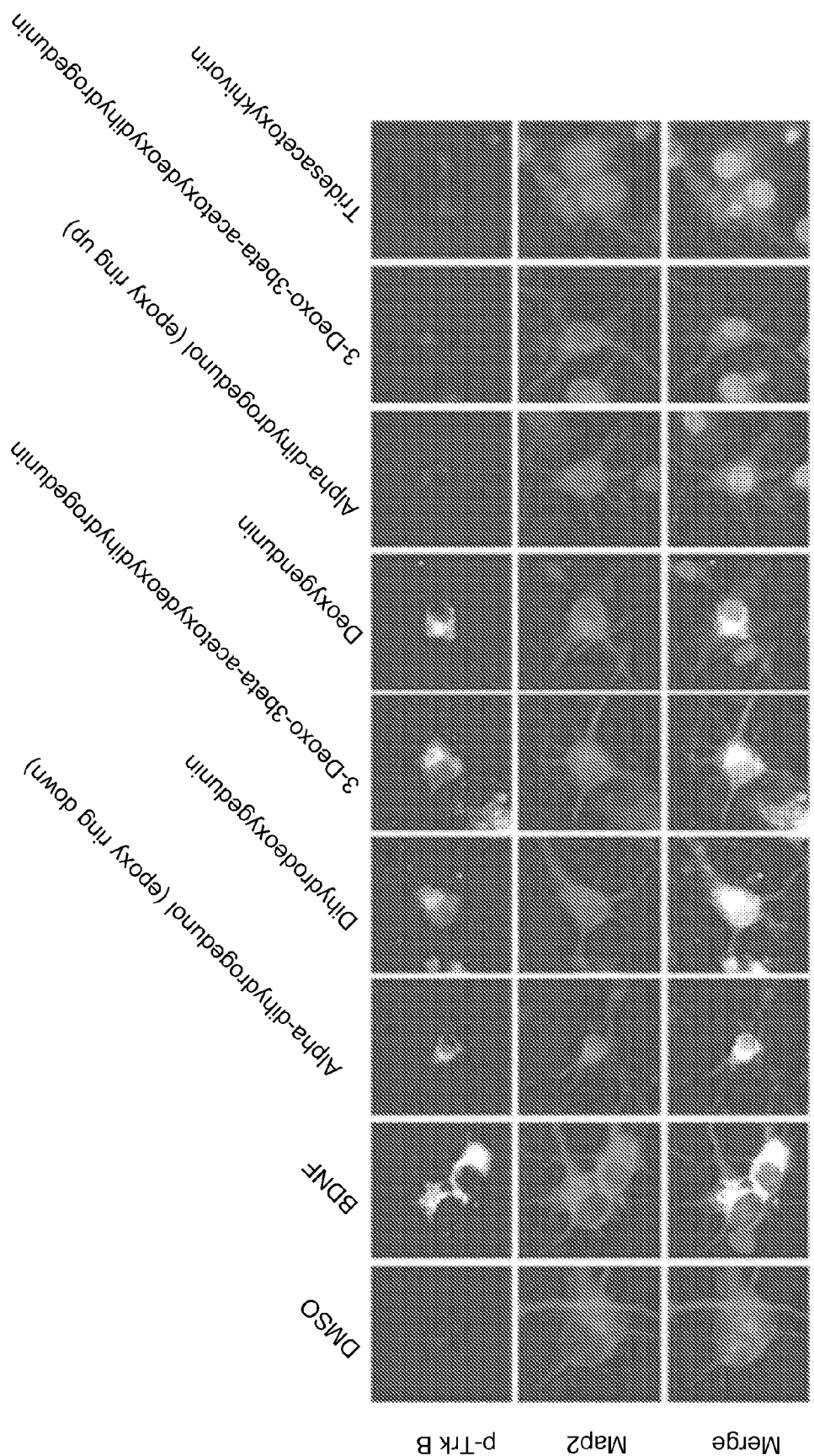
FIG. 5 shows immunofluorescent staining results illustrating neuronal TrkB phosphorylation by various compounds.
Figure 6:
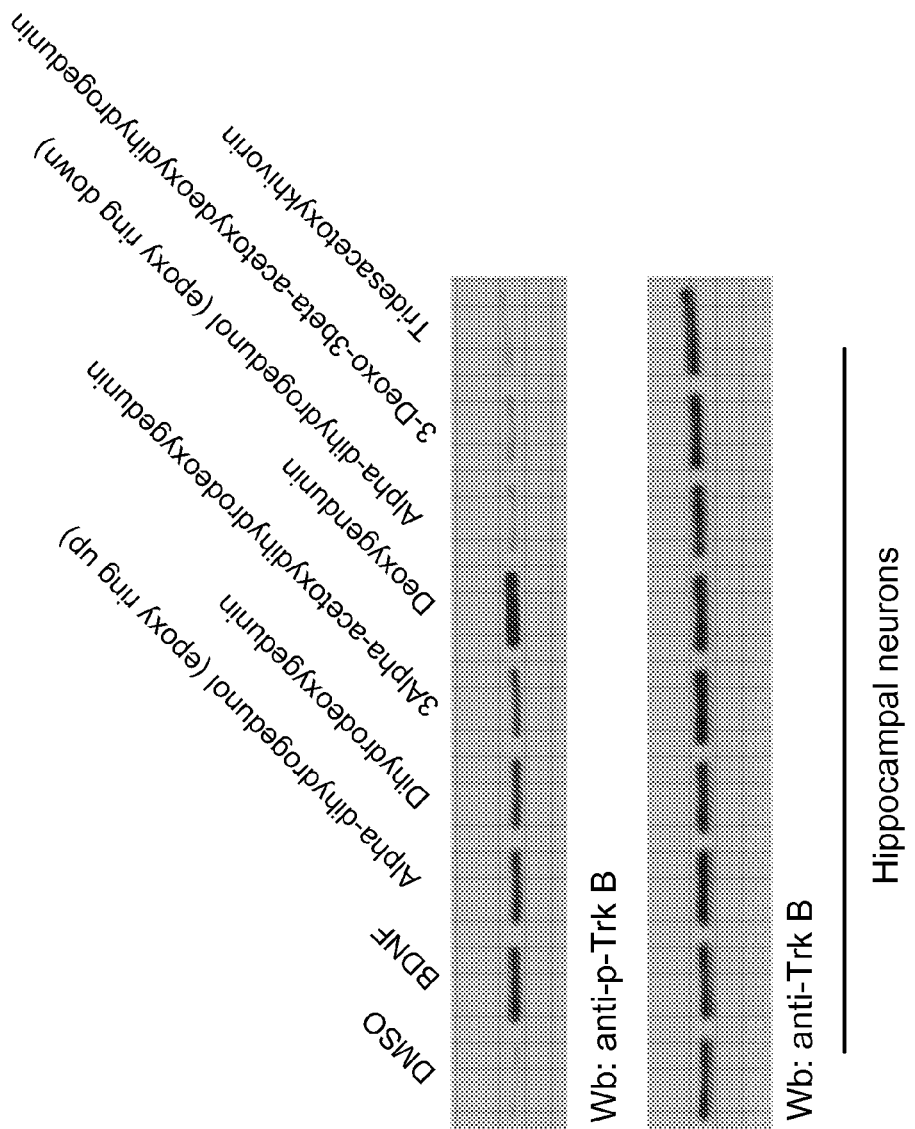
FIG. 6 shows Western blots illustrating TrkB phosphorylation using various compounds.
Figure 7:
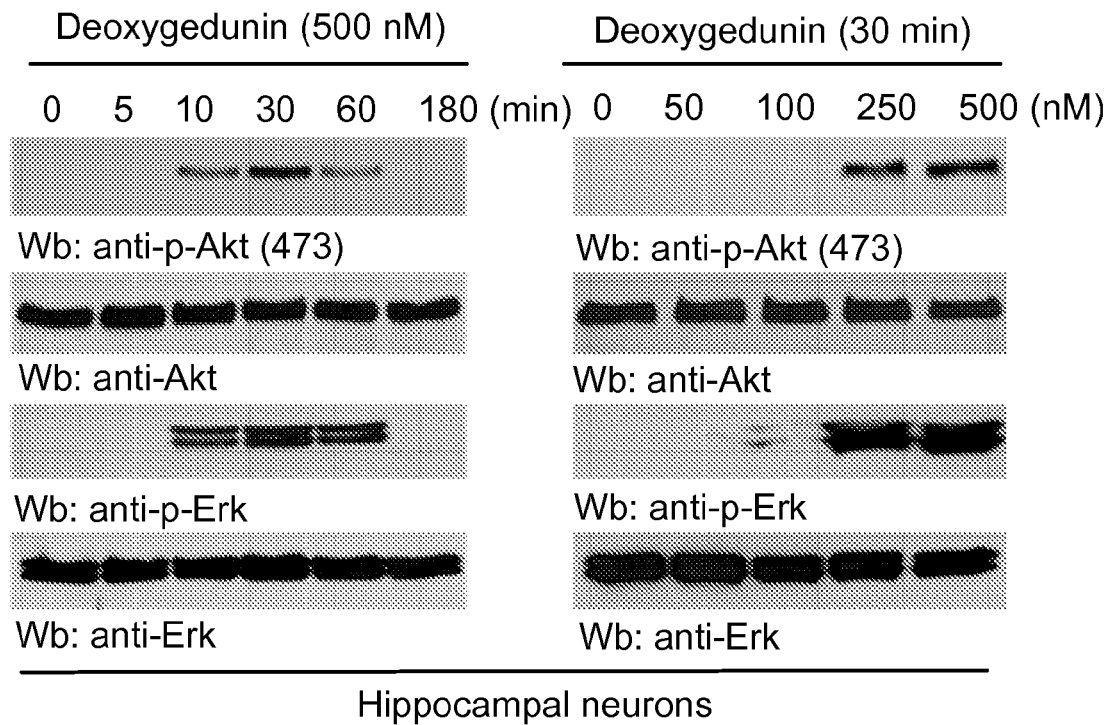
FIG. 7 shows Western blots illustrating activation time (left panels) and dose dependency (right panels) for deoxygedunin activation of Erk1/2 and Akt.
Figure 8:
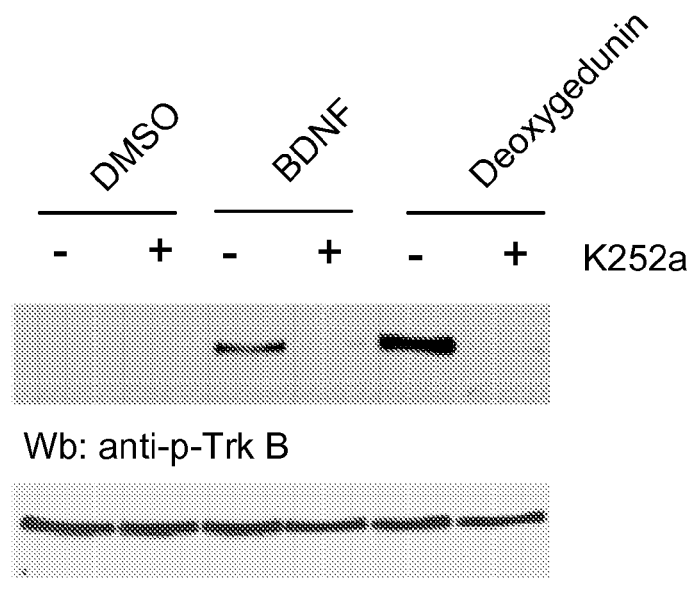
FIG. 8 shows Western blots illustrating deoxygedunin activation of the TrkB receptor.
Figure 9:
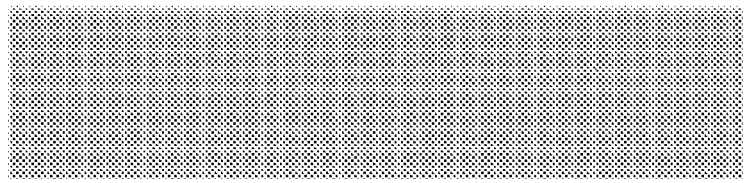
FIG. 9 shows Western blots illustrating TrkB phosphorylation by deoxygedunin over time.
Figure 9:
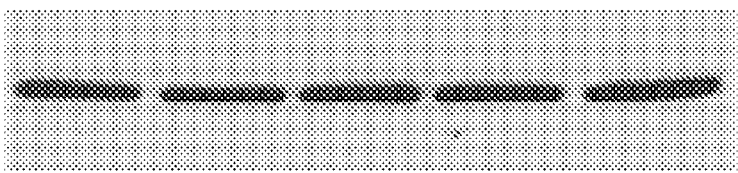
Figure 9:
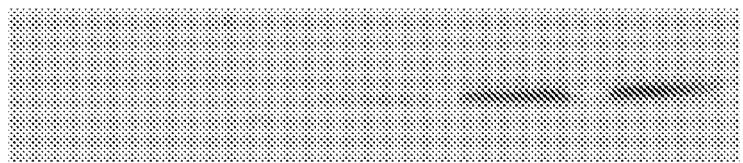
Figure 9:
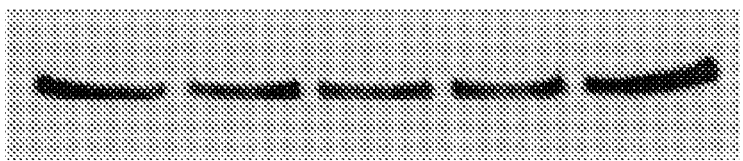
Figure 9:
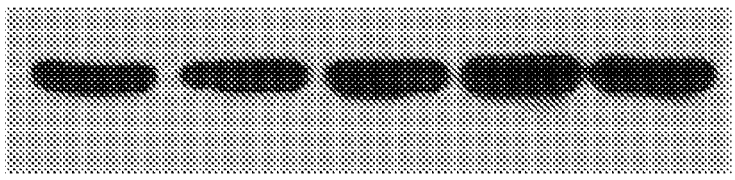
Figure 10:
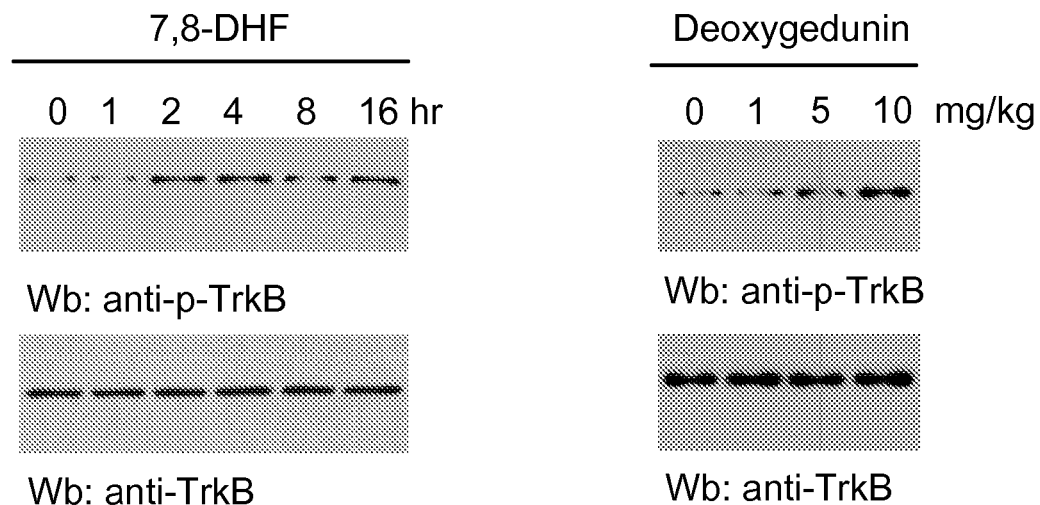
FIG. 10 shows TrkB oral activation in mouse brain by both 8-dihydroxyflavone and deoxygedunin.
Figure 11:
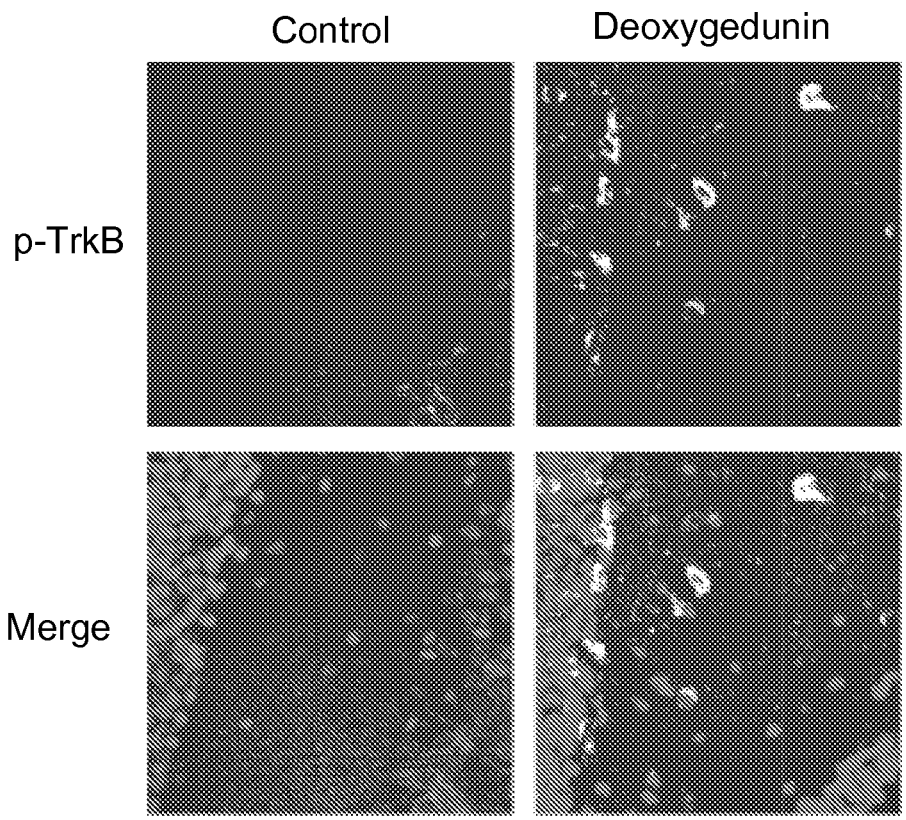
FIG. 11 shows immunofluorescent staining results illustrating TrkB activation by deoxygedunin in the hippocampus.

Deoxygedunin (among others) elicited a strong TrkB phosphorylation (see FIG. 5), which was also independently confirmed by immunoblotting analysis (see FIG. 6). Both Akt and Erk1/2 were robustly activated by these molecules as well). In hippocampal neurons, deoxygedunin prominently provoked both Erk1/2 and Akt activation with a time course (see FIG. 7, left panels) and stimulated both Erk1/2 and Akt activation in a dose dependent manner (see FIG. 7, right panels). The minimal required drug concentration was about 100-250 nM (see FIG. 7, right panels). These data demonstrate that deoxygedunin potently activated TrkB receptor and its downstream Akt and MAP kinases in neurons. To further demonstrate that deoxygedunin activates TrkB receptor, hippocampal neurons were pretreated with K252a (a Trk receptors inhibitor) and TrkB activation was examined (see FIG. 8). As shown in FIG. 8, pretreatment with K252a substantially blocked deoxygedunin-triggered TrkB activation in hippocampal neurons, demonstrating that deoxygedunin can provoke TrkB autophosphorylation. Deoxygedunin-provoked downstream Akt and MAPK signalings were also blocked by K252a. To assess whether deoxygedunin provokes TrkB activation in the brain, mice (i.p.) were injected with a dose of 5 mg/kg for various time points. TrkB but not TrkA was selectively phosphorylated in the brain 2 hours after injection, and peaked at 4-8 hours (see FIG. 9), suggesting that deoxygedunin penetrated the blood-brain barrier and stimulated TrkB activation. To establish that deoxygedunin is orally bioactive in provoking TrkB activation, two to three month old C57BL/6J mice were orally injected with various doses of 7,8-dihydroxyflavone or deoxygedunin then sacrificed 2 to 4 hours after administration. Brain lysates were prepared and analyzed by immunoblotting (see FIG. 10). FIG. 10 shows that TrkB was orally activated in mouse brain by both 8-dihydroxyflavone and deoxygedunin with dosages as low as 1-5 mg/kg. RT-PCR analysis revealed no change of TrkA or TrkB in mouse brain upon deoxygedunin treatment, indicating that deoxygedunin provokes TrkB activation independent of Trk receptor transcriptional alteration. Immunohistochemistry staining demonstrated robust TrkB activation in hippocampus upon deoxygedunin treatment (see FIG. 11). These data demonstrate that deoxygedunin strongly triggered TrkB activation both in vitro and in vivo.

Example 11

Deoxygedunin Binds TrkB ECD and Provokes its Dimerization

Figure 12A:
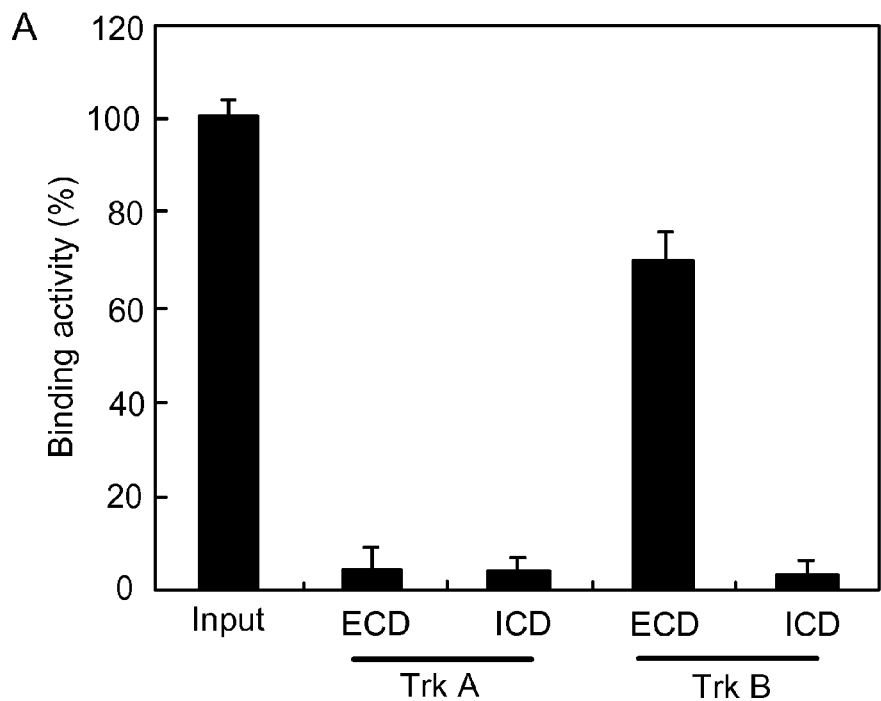
FIGS. 12A (top panel) and 12B (bottom panel) show graphs illustrating binding activity for [$^3$H]-deoxygedunin to various domains of TrkB.
Figure 12B:
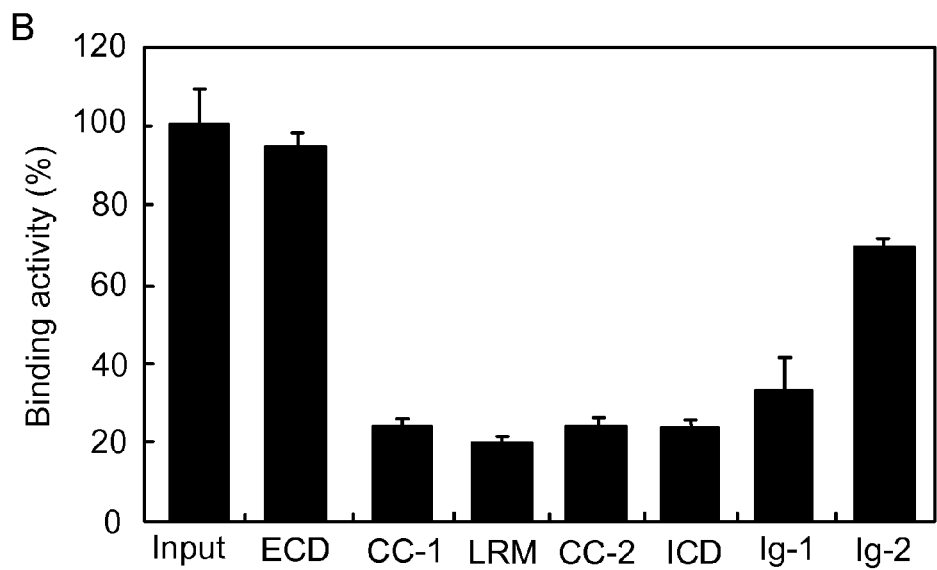
Figure 13:
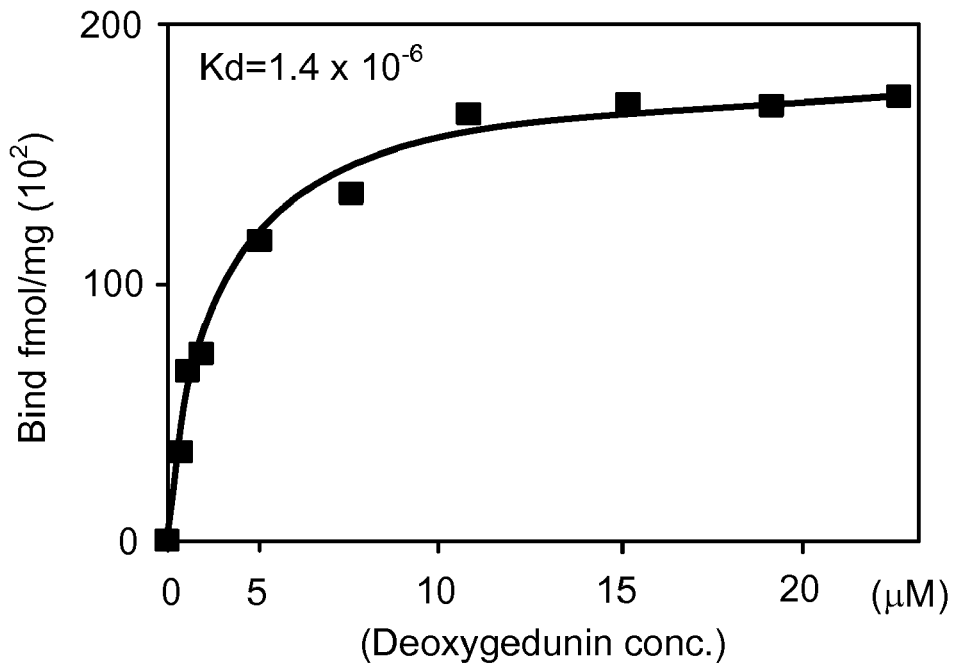
FIG. 13 shows Scatchard plot analysis of deoxygedunin provocation of TrkB dimerization.
Figure 13:
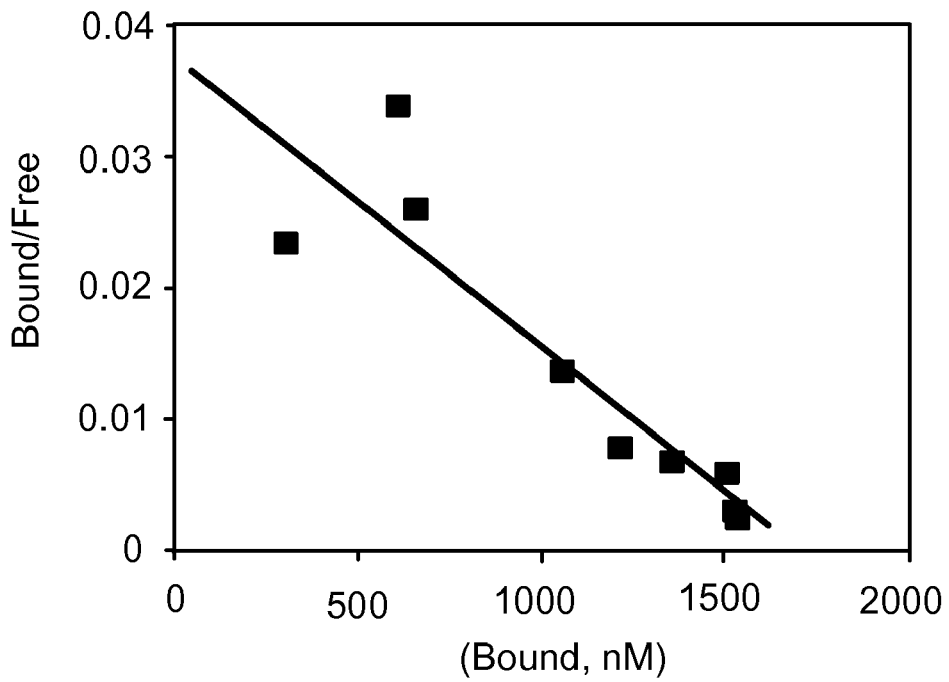
Figure 14:
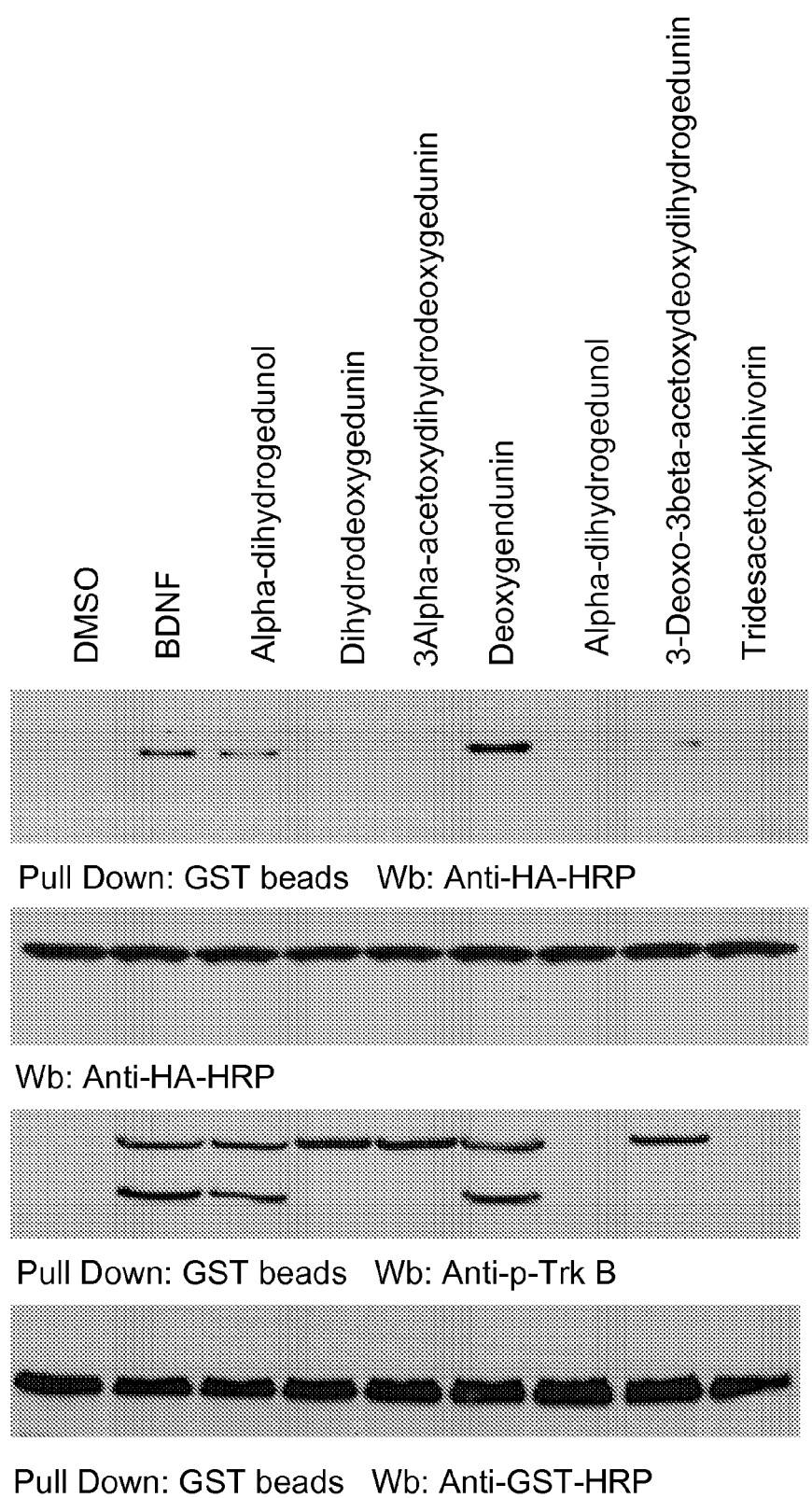
FIG. 14 shows Western blots illustrating the results of a GST pull-down assay for TrkB and various compounds including deoxygedunin.
Figure 15:
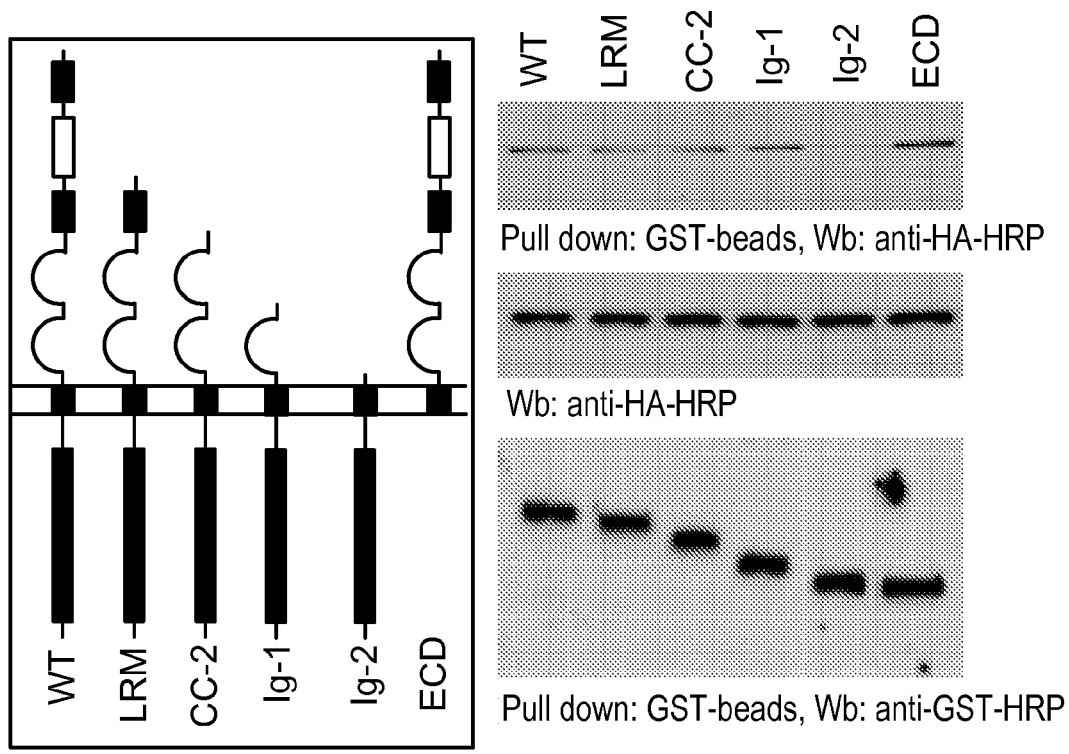
FIG. 15 shows Western blots of a TrkB truncation assay for deoxygedunin binding.
Figure 16:
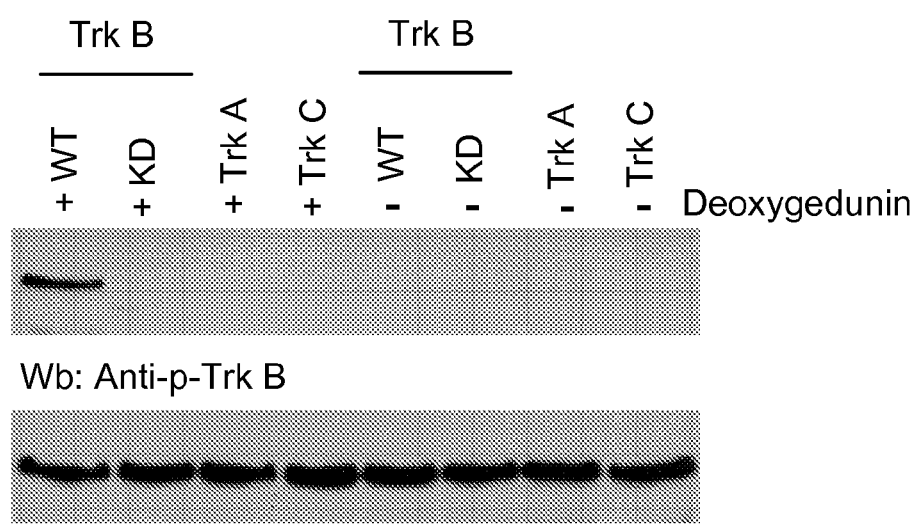
FIG. 16 shows Western blots illustrating that deoxygedunin elicited tyrosine phosphorylation in TrkB but not TrkA or TrkC receptors in transfected HEK293 cells.

To determine whether deoxygedunin binds the intra-cellular domain (ICD) or extra-cellular domain (ECD) of the TrkB receptor, ligand binding assays with [$^3$H]-deoxygedunin were performed. The assays demonstrated that increasing concentrations of [$^3$H]-deoxygedunin progressively bound the TrkB extra-cellular domain (ECD) but not the intra-cellular domain (ICD) (see FIGS. 12A and B). Additionally, [$^3$H]-deoxygedunin did not bind to TrkA, indicating it specifically associated with the extracellular domain of TrkB receptor (see FIG. 12A). Truncation assays showed that the Ig2 domain in the ECD of TrkB was the major binding site for deoxygedunin (FIG. 12B). Scatchard plot analysis revealed that the ratio of ligand to the receptor is 1:1 with binding constant Kd=1.4 µM (FIG. 13). A GST pull-down assay revealed that deoxygedunin robustly provoked TrkB dimerization with an effect even stronger than BDNF (see FIG. 14). Moreover, alpha-dihydrogedunol (epoxy ring down) also notably promoted TrkB dimerization (see FIG. 14), fitting with its stimulatory activity on TrkB (see Example 10). The coprecipitated HA-TrkB was also prominently tyrosine phosphorylated (see FIG. 14, $3^{rd}$ panel). These data indicated that deoxygedunin directly bound TrkB ECD and triggered its association. Truncation assays showed that deletion of Ig2 domain in TrkB diminished its association by deoxygedunin (FIG. 15). Deoxygedunin also elicited tyrosine phosphorylation in TrkB but not in TrkA or TrkC receptor in transfected HEK293 cells. TrkB-KD displayed negligible phosphorylation compared to wild-type TrkB (FIG. 16), indicating that TrkB phosphorylation by deoxygedunin was through the receptor autophosphorylation but not by any other tyrosine kinases. These data showed that deoxygedunin bound to the ECD of TrkB and promoted its association and activation.

Example 12

Deoxygedunin Protects Neurons from Apoptosis in a TrkB-Dependent Manner

Figure 17:
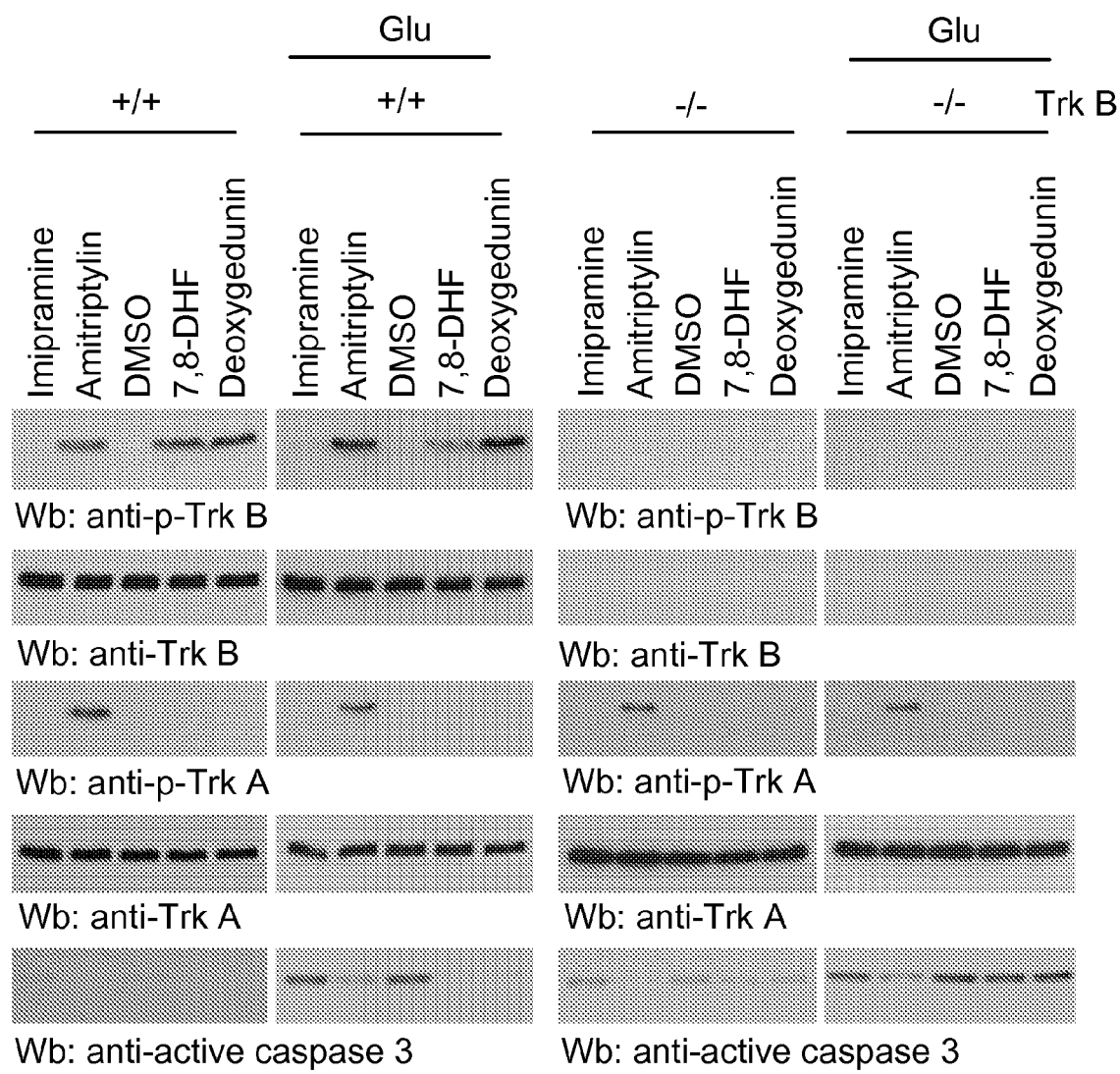
FIG. 17 shows Western blots illustrating TrkA and TrkB activation for various compounds in cortical neurons of TrkB +/+ or −/− mice.
Figure 18:
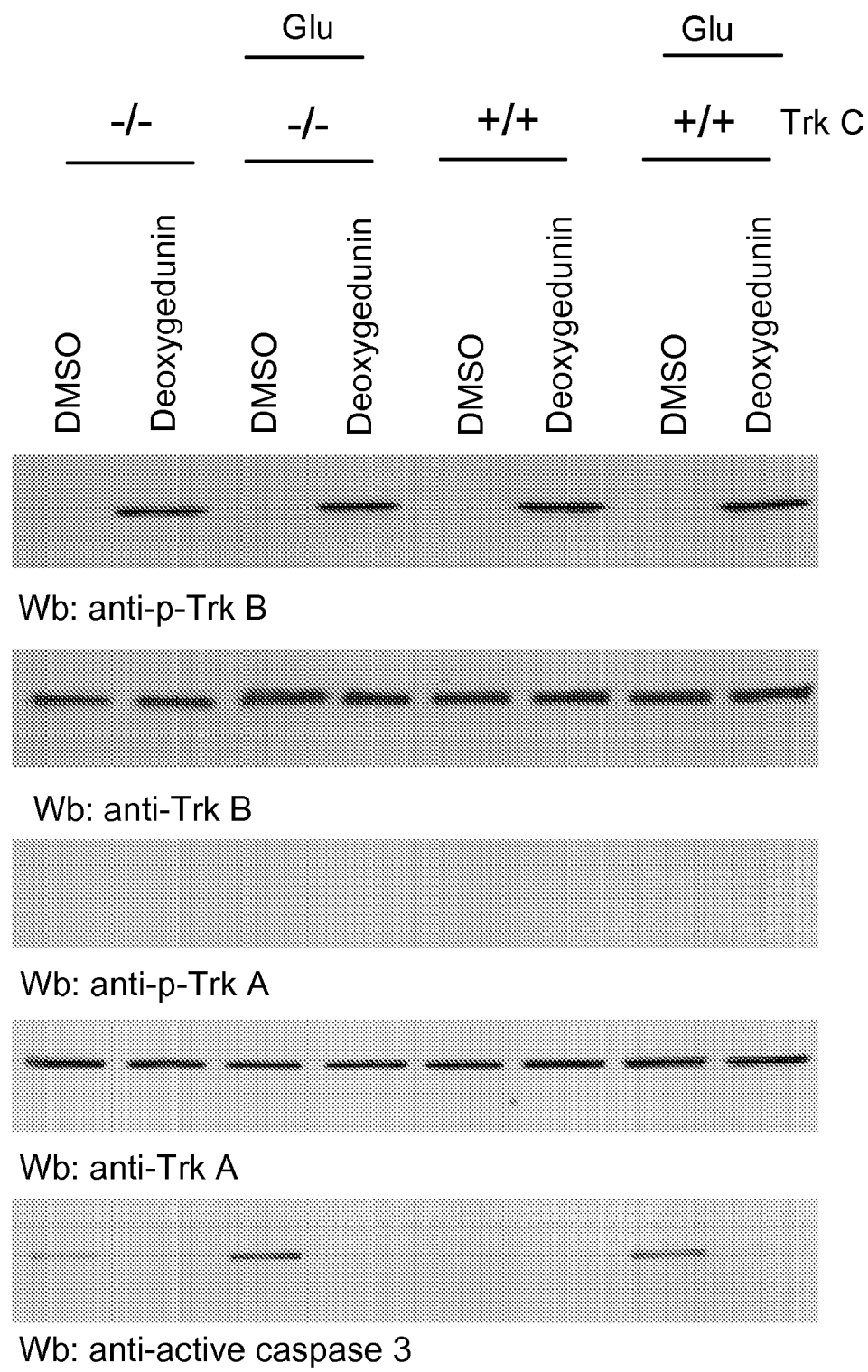
FIG. 18 shows Western blots illustrating deoxygedunin activation of TrkB but not TrkA in both wild-type and TrkC knockout neurons.

To determine if deoxygedunin's neuronal protective effect was mediated through TrkB receptor, cortical neurons from pups of TrkB +/− mice mated to the same genotype were prepared. Deoxygedunin specifically activated TrkB but not TrkA receptor in wild-type but not TrkB −/− neurons. 7,8-dihydroxyflavone (7,8-DHF), another positive compound from the screening, also selectively activated TrkB but not TrkA. The tricyclic antidepressant drugs amitriptyline but not imipramine activated both TrkA and TrkB (FIG. 17, top and 3rd panels). Glutamate-provoked caspase-3 activation was substantially blocked by 7,8-DHF and deoxygedunin in wild-type but not TrkB −/− neurons. However, the control compound imipramine failed to block caspase-3 activation by glutamate. In contrast, amitriptyline weakly suppressed caspase-3 activation in both wild-type and TrkB −/− neurons (FIG. 17, bottom panels). Thus, deoxygedunin selectively suppressed apoptosis triggered by glutamate in a TrkB dependent manner. Moreover, deoxygedunin strongly provoked TrkB but not TrkA activation in both wild-type and TrkC knockout neurons (FIG. 18, top panel). Additionally, the spontaneous caspase-3 activation in TrkC −/− neurons was suppressed by deoxygedunin. Further, glutamate triggered caspase-3 activation was diminished by deoxygedunin (FIG. 18, bottom panel), indicating that it repressed neuronal apoptosis in a TrkB- but not TrkC-dependent.

TrkB F616A was known to be selectively blocked by 1NMPP1 resulting in an effective TrkB-null phenotype (see Chen et al., Neuron 46, 13-21 (2005)). BDNF-provoked TrkB phosphorylation was selectively blocked by 1NMPP1 but not K252a in cortical neurons from TrkB F616A knockin mice (see FIG. 19, top panel).

Figure 19:
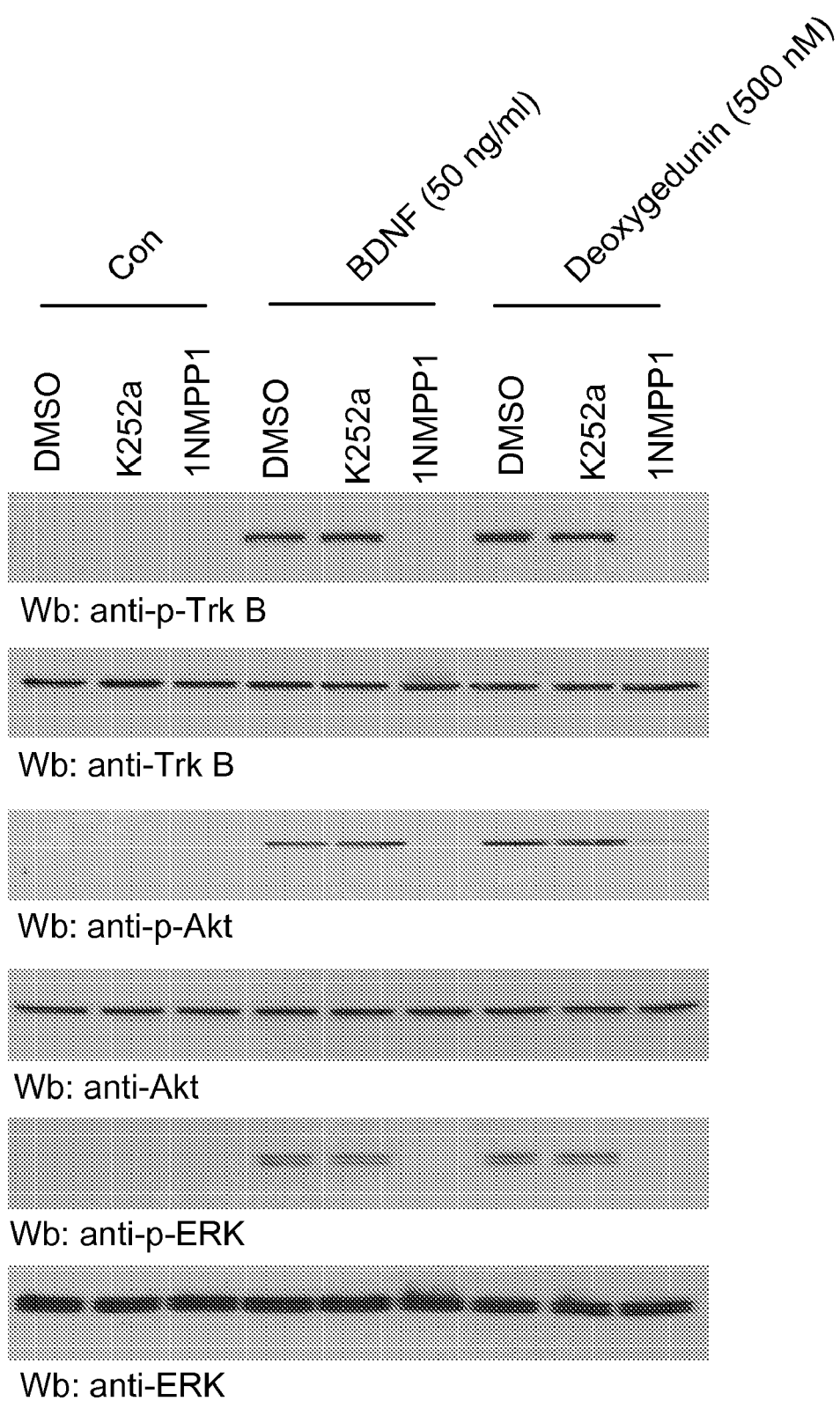
FIG. 19 shows Western blots illustrating the provocation of TrkB phosphorylation by various compounds.
Figure 20:
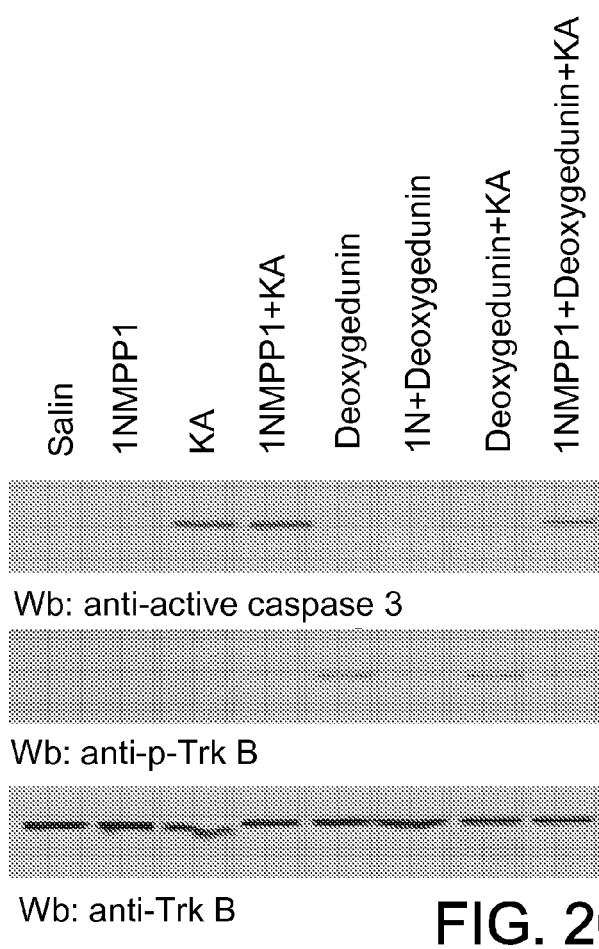
FIG. 20 shows Western blots illustrating the effects of various compounds on KA-provoked apoptosis in TrkB F616A knockin mice.

Similarly, deoxygedunin provoked TrkB phosphorylation was selectively blocked by 1NMPP1 but not K252a in cortical neurons from TrkB F616A knockin mice (FIG. 19, top panel). Additionally, 1NMPP1, but not K252a, blocked BDNF-triggered Akt and Erk1/2 activation. Similarly, 1NMPP1 diminished Akt and Erk1/2 activation by deoxygedunin (FIG. 19, 3rd and 5th panels). 1NMPP1's selective inhibition of TrkB F616A activation by deoxygedunin, suggested that the blockade of TrkB F616A signaling by 1NMPP1 in mice makes the neurons vulnerable to KA-provoked neuronal cell death. KA caused caspase-3 activation, and pretreatment of 1NMPP1 elevated KA-provoked apoptosis in TrkB F616A (see FIG. 20), supporting that TrkB signaling was involved in neuronal survival. Deoxygedunin suppressed KA-provoked apoptosis, whereas 1NMPP1 pretreatment diminished deoxygedunin's protective effect in F616A mice. TrkB activation status inversely correlated with TrkB activation by deoxygedunin (FIG. 20, top and middle panels). These data show that deoxygedunin selectively activated TrkB receptor and enhanced neuronal survival in mice in TrkB dependent manner.

Example 13

Figure 21:
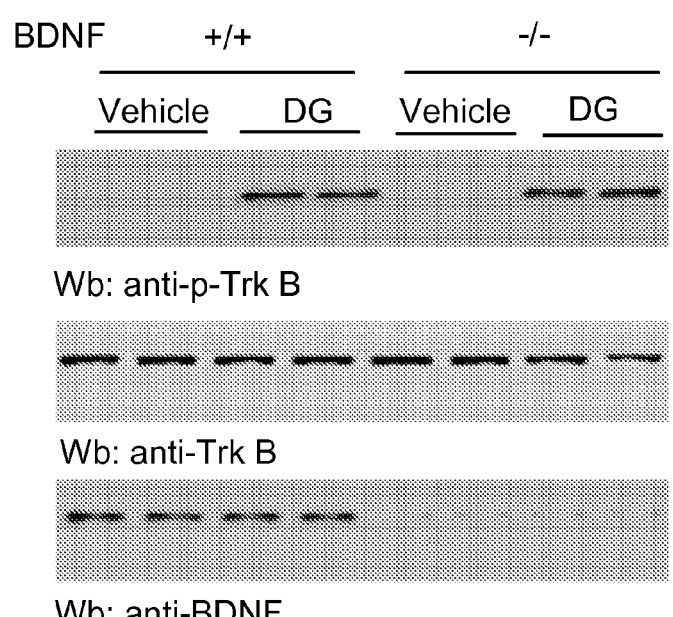
FIG. 21 shows Western blots illustrating TrkB activation by deoxygedunin in wild-type and BDNF −/− mice.
Figure 22:
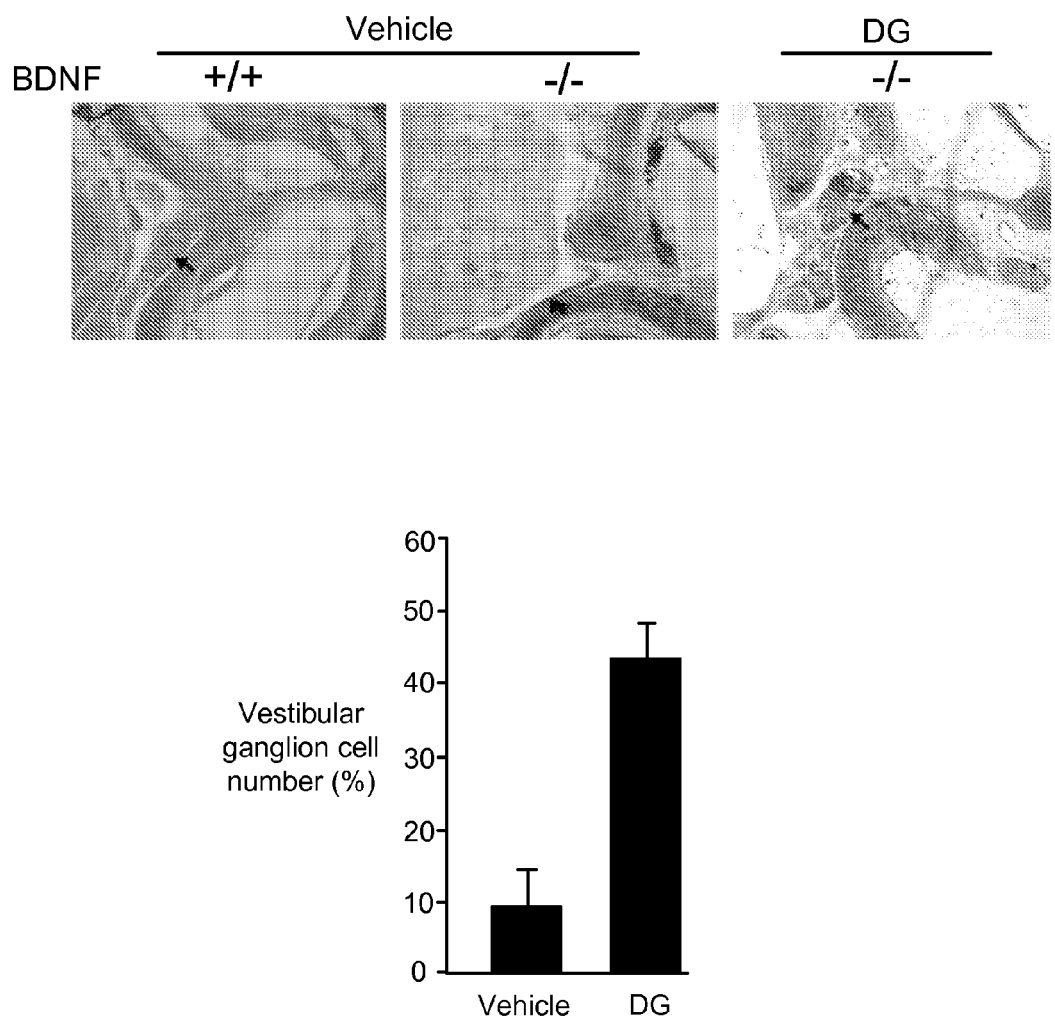
FIG. 22 shows stained inner ear sections from BDNF +/+ and −/− mice treated with vehicle or deoxygedunin (left three panels) and the right panel shows a graph indicating vestibular ganglion cell number in deoxygedunin (DG) and vehicle treated BDNF −/− pups.

Deoxygedunin Activates TrkB in BDNF Independent Manner and Prevents Vestibular Ganglion Loss To examine whether deoxygedunin activating TrkB involved endogenous BDNF, BDNF conditional knockout mice with BDNF gene deletion limited to cortex (thus allowing normal development) were used. Deoxygedunin (5 mg/kg) was intraperitoneally injected into the BDNF cortex conditional knockout mice and the mice were sacrificed at 4 hours. TrkB activation occurred in both wild-type and BDNF −/− mice (see FIG. 21), demonstrating that deoxygedunin activated TrkB independent of BDNF. Mutant mice lacking BDNF were known to have severe deficiencies in coordination and balance, which have been associated with excessive degeneration in several sensory ganglia including the vestibular ganglion (Ernfors et al., Nature 368, 147-150 (1994)). To determine whether deoxygedunin rescued this loss of vestibular ganglions in BDNF −/− pups, conventional BDNF +/− mice were bred with the same genotype mice. Deoxygedunin (5 mg/kg, i.p.) was administered to the pregnant mice at day E7.5 until birth. The neonatal pups continued receiving the same dose of deoxygedunin, but BDNF −/− pups continued dying at P1 or P2. Staining of inner ear sections showed that vestibular ganglia were completely lost in most of control vehicle-treated BDNF −/− pups. In contrast, many of deoxygedunin-treated BDNF mutant mice displayed intact vestibular ganglia, similar to the wild-type pups (see FIG. 22, left three panels). Quantitative analysis demonstrated that 9.1±4.9% of vestibular ganglia were detected in vehicle-treated BDNF −/− pups, whereas deoxygedunin treatment increased to 42.2±6.3% (see FIG. 22, right panel). These data show that deoxygedunin mimicked BDNF and significantly protected vestibular ganglia from degeneration in BDNF −/− pups.

Example 14

Deoxygedunin has an Antidepressant Effect

Figure 23A:
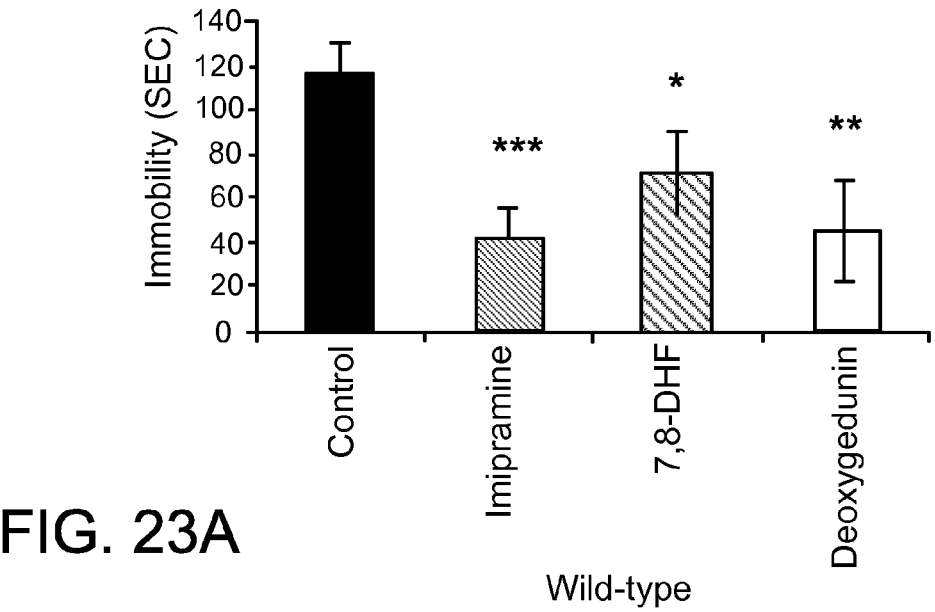
FIGS. 23A and 23B show graphs illustrating the effect of various compounds on mouse immobility in forced swim tests.
Figure 23B:
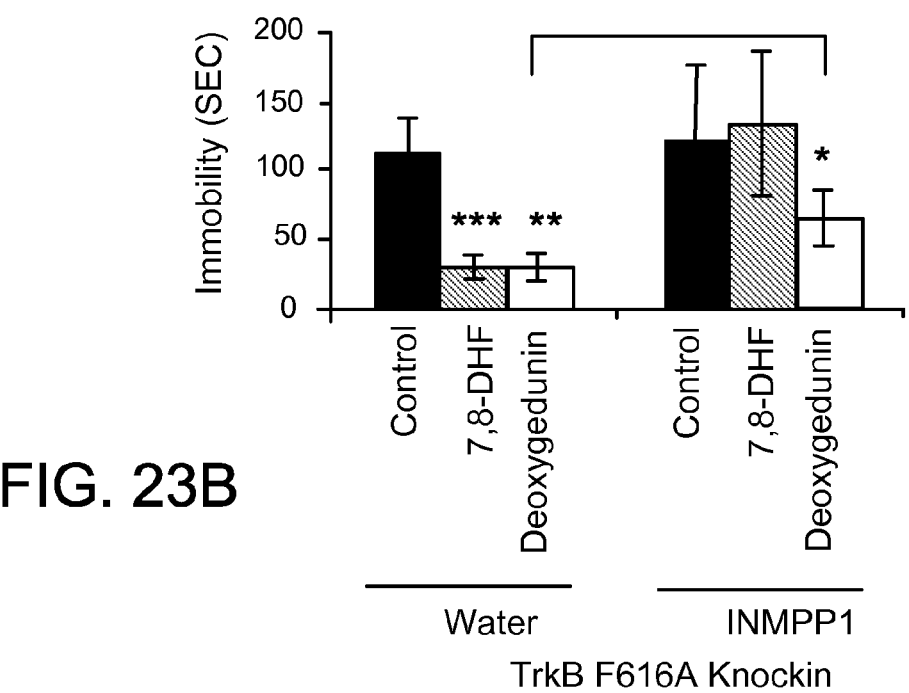

To investigate whether deoxygedunin mimicked BDNF in suppressing depression-like symptoms, a forced swim test after subchronic treatment of the mice for 5 days with various drugs was conducted. When mice were treated with imipramine (20 mg/kg), a tricyclic antidepressant drug, the swimming immobility was significantly decreased. Deoxygedunin (5 mg/kg) also reduced the immobility (see FIG. 23A). To assess whether the behavior responses by 7,8-DHF and deoxygedunin were mediated by TrkB receptor, TrkB F616A knockin mice were used. The transgenic mice were subjected to saline or 1NMPP1 treatment, respectively. No significant difference was observed in the immobility time between saline and 1NMPP1-treated mice. In the saline group, deoxygedunin substantially reduced the immobility time; however, deoxygedunin did not have a significant effect in mice when TrkB was blocked by 1NMPP1 (see FIG. 23B), suggesting that inhibition of the TrkB signaling cascade inhibited the antidepressant effect of deoxygedunin. Thus, these data show that deoxydegunin mimicked BDNF and acted as a potent antidepressant drug in mice through activating the TrkB receptor.

Example 15

Deoxygedunin Displays Therapeutic Effects on Various Neurological Disorders

Figure 24:
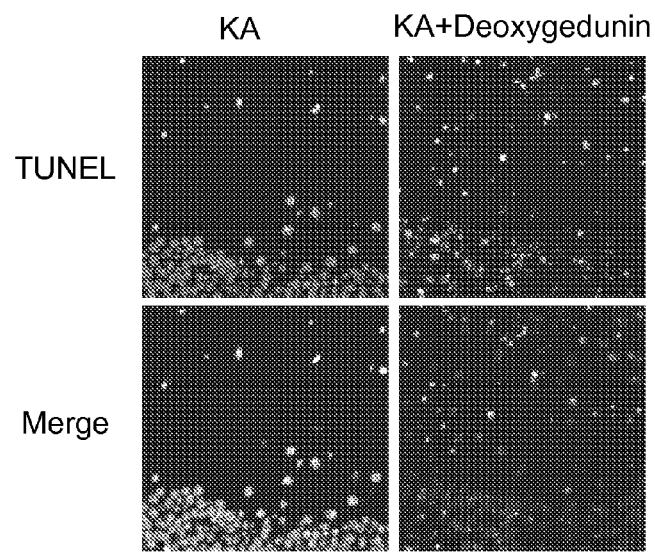
FIG. 24 shows TUNEL staining images illustrating that KA provoked apoptosis is diminished by deoxygedunin in C57BL/6 mice.
Figure 24:
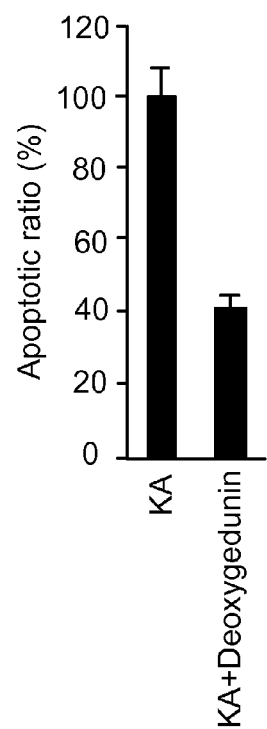
Figure 25:
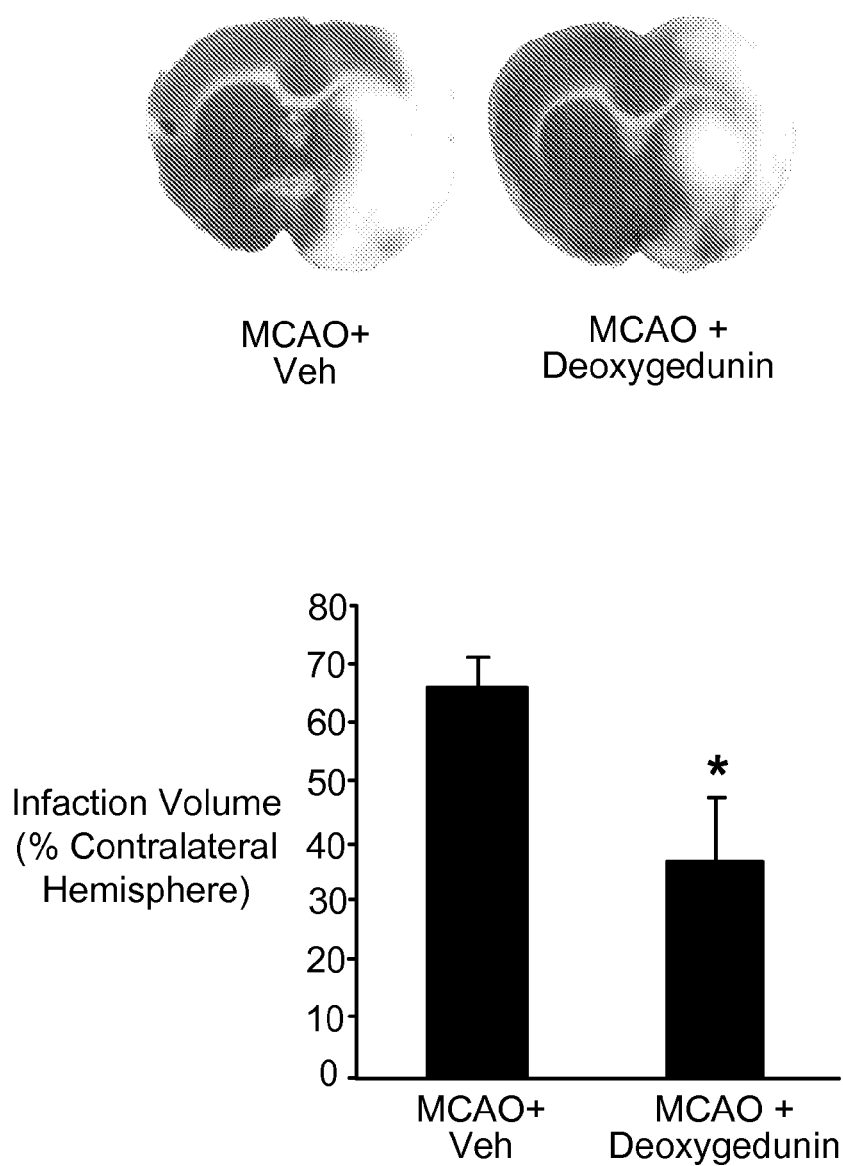
FIG. 25 shows representative TTC stained brain slices 24 hours after MCAO for vehicle-treated and deoxygedunin-treated rats.

Kainic acid (KA), a specific agonist for the kainate receptor, was known to induce neuronal cell death in caspase-dependent and independent manners. To explore whether deoxygedunin can block the neurotoxicity initiated by KA, 5 mg/kg deoxygedunin was intraperitoneally injected into C57BL/6 mice, followed by 20 mg/kg KA. In 5 days, the mice were perfused and the brains were cut to a thickness of 5 μm and mounted on slides. TUNEL staining revealed that KA provoked apoptosis in the hippocampus, but that apoptosis was diminished by deoxygedunin (FIG. 24, left panel). Quantitative analysis of apoptosis in the hippocampus revealed that deoxygedunin decreased KA induced apoptosis in hippocampus by 60% (FIG. 24, right panel). To further determine the neuroprotective potential in vivo, deoxygedunin was tested in a transient middle cerebral artery occlusion (MCAO) stroke model in adult male rats. After 2 h MCAO followed by reperfusion, the animals received vehicle or deoxygedunin (5 mg/kg) 5 minutes prior to the onset of reperfusion. All animals included in the study survived the ischemic insult and treatment with deoxygedunin. Representative brain slices stained with TTC 24 hours after MCAO for vehicle-treated and deoxygedunin-treated rats are shown in FIG. 25 (left panel). Area and volume measurements from the TTC stained sections indicated that treatments with deoxygedunin significantly reduced infarct volumes in this transient ischemic model of stroke (FIG. 25, right panel). These results indicated that pretreatment with intraventricular BDNF reduced infarct size after focal cerebral ischemia in rats and supported the hypothesis of a neuroprotective role for BDNF in stoke. Taken together, these data indicated that deoxygedunin prevented neuronal cell death and was protective of the neurodegeneration elicited by excitatory neurotoxicity and stroke.

Example 16

Figure 26:
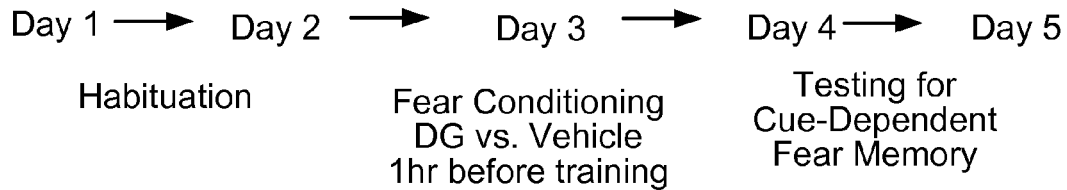
FIG. 26 shows a tone-shock fear conditioning model developed for these studies.
Figure 27:
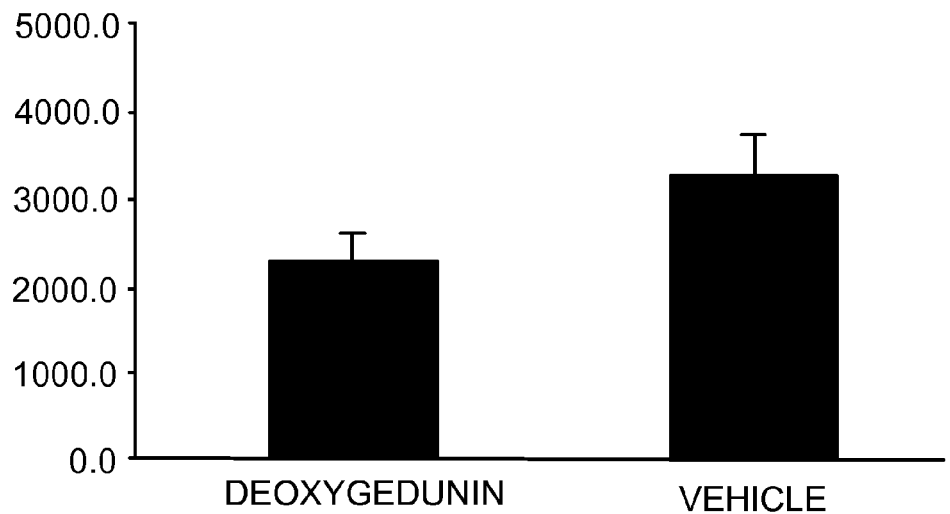
FIG. 27 shows a graph illustrating no difference between vehicle and deoxygedunin treated groups in shock reactivity during fear acquisition training.
Figure 28:
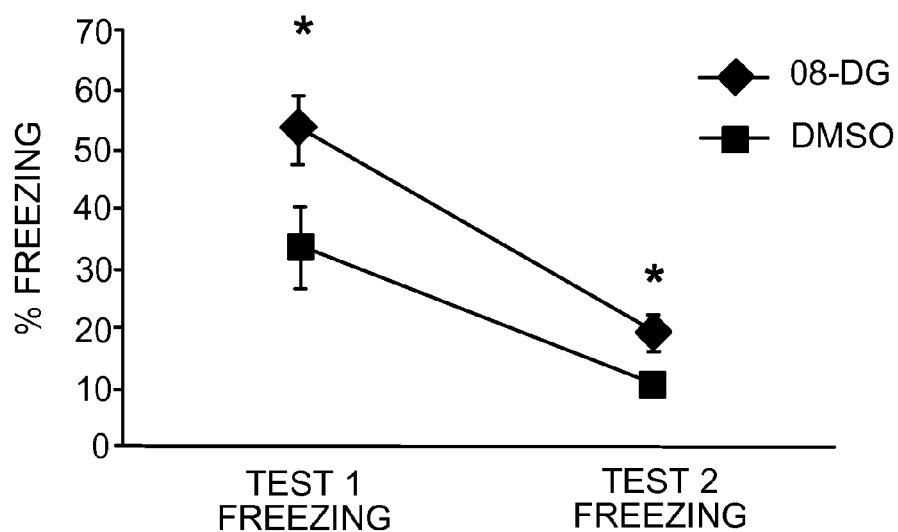
FIG. 28 shows a graph illustrating the difference in tone-dependent conditioned freezing on different testing days between vehicle and deoxygedunin treated mice.
Figure 29A:
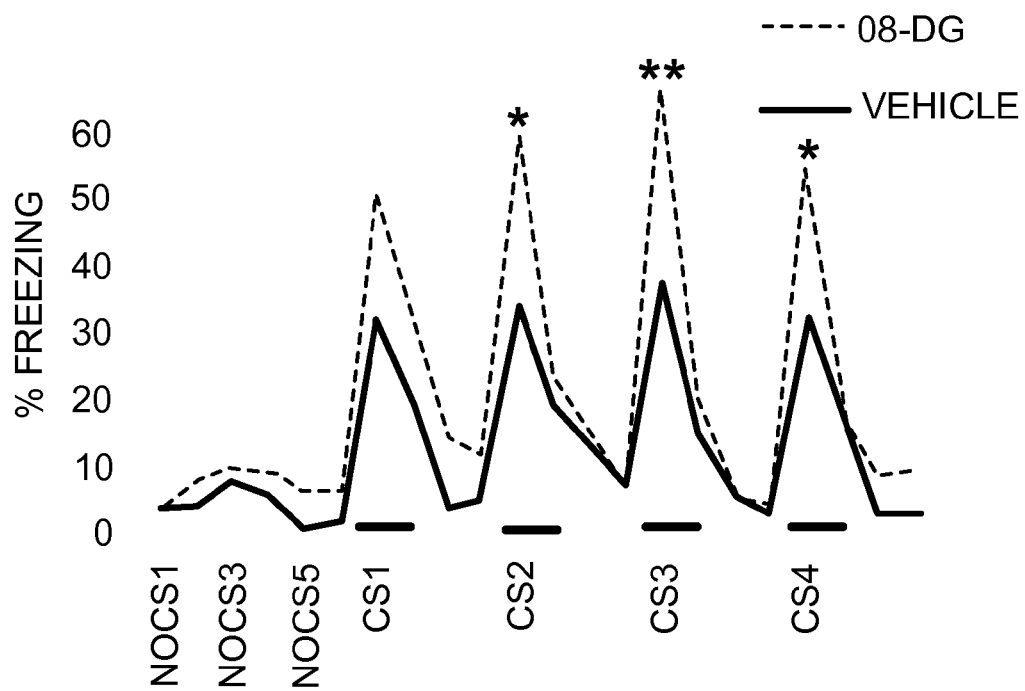
FIGS. 29A and 29B show graphs illustrating the enhanced acquisition or consolidation of fear memory in deoxygedunin treated mice.
Figure 29B:
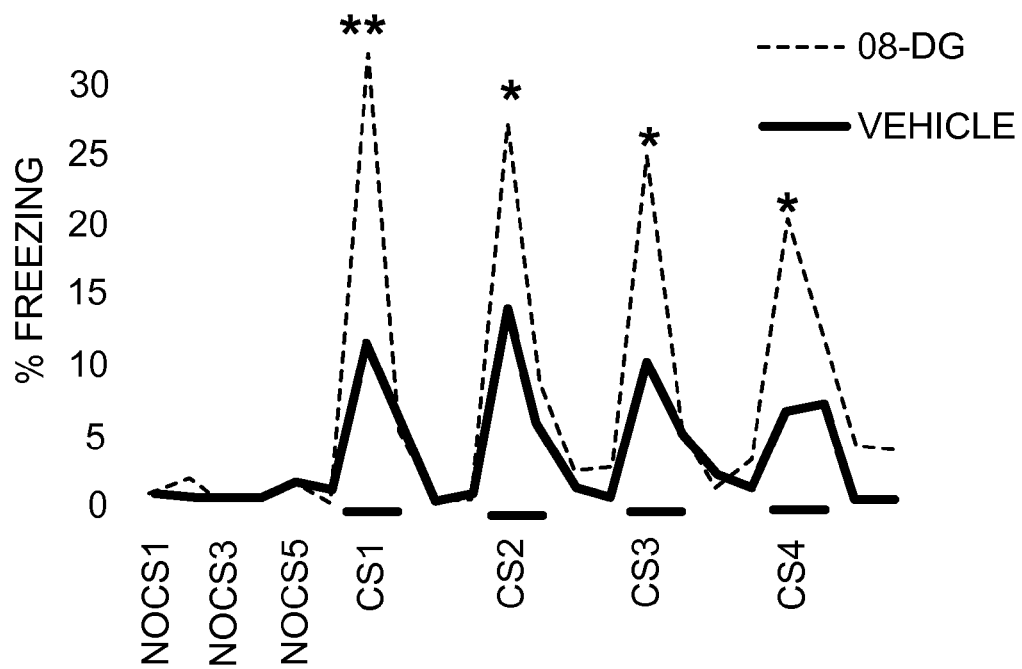

Deoxygedunin Enhances Acquisition of Conditioned Fear, a BDNF-Dependent Learning Process To determine whether deoxygeduning would enhance learning in a whole animal model of learning and memory, in which BDNF-dependent TrkB activation was required, a tone-shock fear conditioning model was developed (see FIG. 26). Following habituation to the testing context, 28 adult wild-type, C57BL/6J mice were given systemic injections of deoxygedunin (N=14, 5 mg/kg, i.p.) or vehicle (N=14) 1 hour prior to being subjected to the tone-shock fear conditioning model. There was no difference between treatment groups in shock reactivity during the fear acquisition training, suggesting that there were no acute effects on pain sensitivity that would affect fear acquisition or later fear expression (p>0.1; see FIG. 27). Mice were then tested, with no additional drug treatment, for cue-conditioned fear in the previously habituated context on the two days following fear acquisition. The average level of tone-dependent conditioned freezing was significantly different on both testing days (see FIG. 28; repeated measures ANOVA, $F(1,26)=6.6$, $p=0.016$) suggesting that mice that received deoxygedunin at the time of training had enhanced acquisition or consolidation of the fear memory. To further explore these effects, individual animals' freezing levels throughout the tone-fear testing sessions were examined. On both testing day 1 (see FIG. 29A) and day 2 (see FIG. 29B), the enhancement in freezing only corresponded with the periods of tone cue presentation. The mice demonstrated similar levels of locomotor exploratory activity prior to and in-between tone exposure in this context, but the animals that received deoxygedunin during the previous tone-shock fear conditioning demonstrated increased freezing during cued fear presentations (Day 1, repeated measures ANOVA of first 4 CS trials, $F(1,26)=8.1$, $p<0.01$; Day 2, $F(1,26)=7.5$, $p<0.01$). This increase in fear learning led to a 2-3 fold increase in the level of freezing during the first set of conditioned stimulus (CS) trials examined each day. Together, these results suggested that although deoxygedunin neither affected apparent level of pain or shock reactivity during training nor affected general locomotor activity in the testing situation on subsequent days, the learning event that occurred during training in the presence of systemic deoxygedunin compared with vehicle was acquired or consolidated in a more effective manner. Since cue-dependent fear conditioning was known to require, and be exquisitely sensitive to, BDNF activation of TrkB, these data were consistent with deoxygedunin acting on the TrkB system in vivo to enhance cue-dependent fear learning.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus a combination of steps, elements, components, or constituents may be explicitly mentioned herein; however, all other combinations of steps, elements, components, and constituents are included, even though not explicitly stated.

What is claimed is:

1. A method of treating or reducing the risk of depression in a subject, comprising:
   selecting a subject with or at risk of developing depression; and
   administering to the subject a therapeutically effective amount of the compound of the following formula:

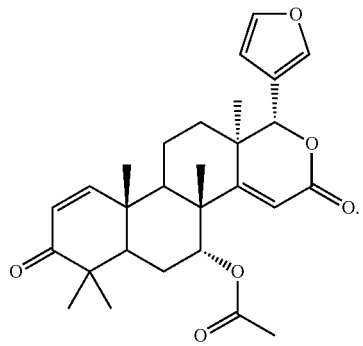

2. The method of claim 1, wherein the compound is administered in combination with an anti-depressant.

* * * * *